US012791559B2

(12) United States Patent
Zhou et al.

(10) Patent No.: US 12,791,559 B2
(45) Date of Patent: Nov. 10, 2026

(54) METHOD AND APPARATUS FOR MAGNETICALLY SORTING RARE CELLS

(71) Applicant: Applied Cells Inc., Santa Clara, CA (US)

(72) Inventors: Yuchen Zhou, San Jose, CA (US); Silin Sa, San Jose, CA (US); Liping Yu, San Jose, CA (US)

( * ) Notice: Subject to any disclaimer, the term of this patent is extended or adjusted under 35 U.S.C. 154(b) by 482 days.

(21) Appl. No.: 18/396,515

(22) Filed: Dec. 26, 2023

(65) Prior Publication Data

US 2024/0183854 A1 Jun. 6, 2024

Related U.S. Application Data

(63) Continuation-in-part of application No. 18/144,447, filed on May 8, 2023, now Pat. No. 12,544,769, which is a continuation-in-part of application No. 18/111,486, filed on Feb. 17, 2023, which is a continuation-in-part of application No. 18/072,362, filed on Nov. 30, 2022, which is a continuation-in-part of application No. 16/729,398, filed on Dec. 29, 2019, now Pat. No. 11,571,696, which is a continuation-in-part of application No. 15/911,115, filed on Mar. 3, 2018, now Pat. No. 12,145,151.

(60) Provisional application No. 63/406,437, filed on Sep. 14, 2022.

(51) Int. Cl.
*G01N 33/569* (2006.01)
*G01N 33/543* (2006.01)
*G01N 33/575* (2026.01)

(52) U.S. Cl.
CPC . *G01N 33/56972* (2013.01); *G01N 33/54326* (2013.01); *G01N 33/5759* (2026.01); *G01N 2333/70596* (2013.01)

(58) Field of Classification Search
None
See application file for complete search history.

(56) References Cited

U.S. PATENT DOCUMENTS

| | | | |
|---|---|---|---|
| 5,705,059 | A | 1/1998 | Miltenyi |
| 5,711,871 | A | 1/1998 | Miltenyi |
| 6,254,830 | B1 | 7/2001 | Pivarnik et al. |
| 6,417,011 | B1 | 7/2002 | Miltenyi |
| 6,602,422 | B1 | 8/2003 | Miltenyi et al. |
| 7,348,185 | B2 | 3/2008 | Yamamichi |
| 7,474,184 | B1 | 1/2009 | Humphries et al. |
| 7,781,202 | B2 | 8/2010 | Yamamichi |
| 8,114,683 | B2 | 2/2012 | Zhou |
| 8,513,029 | B2 | 8/2013 | Zhou |
| 8,636,906 | B2 | 1/2014 | Stein |
| 8,956,536 | B2 | 2/2015 | Yu et al. |
| 8,986,944 | B2 | 3/2015 | Yamanishi et al. |
| 9,217,131 | B2 | 12/2015 | Lamish et al. |
| 9,513,205 | B2 | 12/2016 | Yu et al. |
| 9,551,643 | B2 | 1/2017 | Warner et al. |
| 9,835,540 | B2 | 12/2017 | Yu et al. |
| 9,885,642 | B2 | 2/2018 | Yu |
| 10,045,913 | B2 | 8/2018 | Warner et al. |
| 10,444,125 | B2 | 10/2019 | Yu |
| 10,620,212 | B2 | 4/2020 | Miltenyi et al. |
| 10,677,695 | B2 | 6/2020 | Koyata et al. |
| 2006/0240572 | A1 | 10/2006 | Carron et al. |
| 2007/0182517 | A1 | 8/2007 | Humphries et al. |
| 2008/0302732 | A1 | 12/2008 | Soh et al. |
| 2009/0065359 | A1 | 3/2009 | Zhou |
| 2010/0317093 | A1 | 12/2010 | Turewicz et al. |
| 2012/0100546 | A1 | 4/2012 | Lowery et al. |
| 2012/0122731 | A1 | 5/2012 | Soh et al. |
| 2012/0295302 | A1 | 11/2012 | Lamish et al. |
| 2013/0265054 | A1 | 10/2013 | Lowery et al. |
| 2013/0266944 | A1 | 10/2013 | Neely et al. |
| 2013/0330739 | A1 | 12/2013 | Yu |
| 2014/0120570 | A1 | 5/2014 | Yu et al. |
| 2015/0010939 | A1 | 1/2015 | Warner et al. |

(Continued)

FOREIGN PATENT DOCUMENTS

| | | | | |
|---|---|---|---|---|
| WO | WO 03044528 | * 8/2002 | ............. | G01N 33/53 |
| WO | 2009132151 | 10/2009 | | |
| WO | WO 2020006404 | * 1/2020 | ............. | G01N 33/50 |

OTHER PUBLICATIONS

Adams et al., Integrated acoustic and magnetic separation in microfluidic channels, Applied Physics Letters, 2009, 254103, vol. 95.
Benez et al., Detection of circulating melanoma cells by immunomagnetic cell sorting, Journal of Clinical Laboratory Analysis, 1999, 229-233, vol. 13.
Iinuma et al., Detection of tumor cells in blood using CD45 magnetic cell separation followed by nested mutant allele-specific amplification of p53 and K-ras genes in patients with colorectal cancer, International Journal of Cancer, 2000, 337-344, vol. 89.
Xia et al., Combined microfluidic-micromagnetic separation of living cells in continuous flow, Biomedical Microdevices, 2006, 299-308, vol. 8.

(Continued)

*Primary Examiner* — Ann Montgomery

(57) ABSTRACT

A method for magnetically sorting rare cells including the steps of (a) flowing a first fluid sample, which contains a first mixture of non-target and magnetically labeled target cells, unimpeded through a conduit of a magnetic separator device at a first flow rate to deposit on a conduit wall a second mixture of non-target and magnetically labeled target cells having a higher purity of the magnetically labeled target cells; (b) recovering the second mixture from the conduit wall by eluting with a buffer fluid to form a second fluid sample; repeating steps (a) and (b) at least one more time using the second fluid sample and a second flow rate to produce a third fluid sample containing a third mixture of non-target and magnetically labeled target cells having a higher purity than the second mixture, wherein the second flow rate is greater than the first flow rate.

20 Claims, 13 Drawing Sheets

(56) References Cited

U.S. PATENT DOCUMENTS

| | | | |
|---|---|---|---|
| 2015/0177111 | A1 | 6/2015 | Warner et al. |
| 2016/0252445 | A1 | 9/2016 | Yu et al. |

OTHER PUBLICATIONS

Pamme et al., Continuous sorting of magnetic cells via on-chip free-flow magnetophoresis, Lab on a Chip, 2006, 974-980, vol. 6.
Kekarainen et al., Optimization of immunomagnetic separation for cord blood-derived hematopoietic stem cells, BMC Cell Biology 7, 30 (2006). https://doi.org/10.1186/1471-2121-7-30.
Hasan et al., Isolation of human blood progenitor and stem cells from peripheral blood by magnetic bead, Bio-Protocol, 2012, vol. 2. http://www.bio-protocol.org/e281.
Zborowski et al., Rare Cell Separation and Analysis by Magnetic Sorting, Analytical Chemistry, 2011, 8050-8056, vol. 83.
Isolation of CD34+ cells from human cord blood, STEMCELL Technologies Inc., 2015.

* cited by examiner

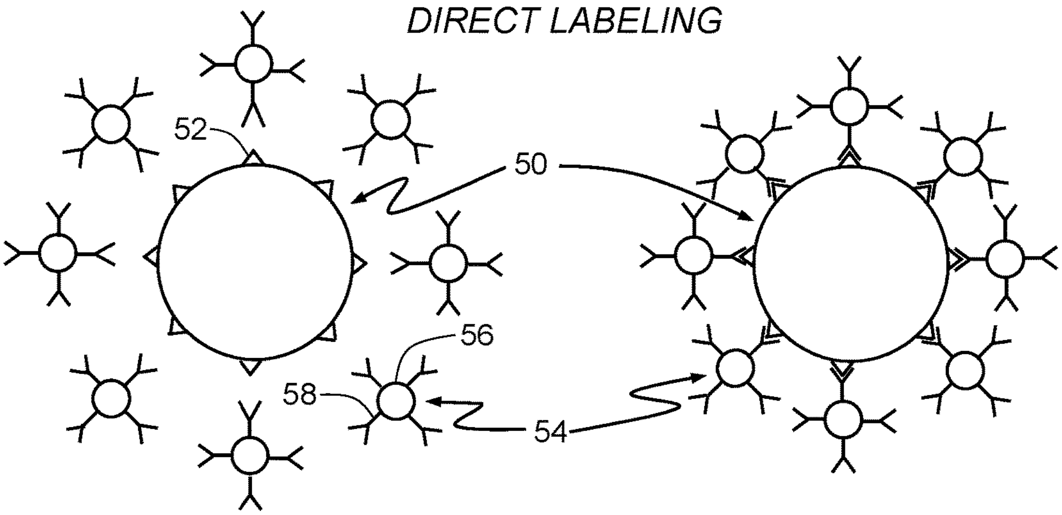
FIG. 1A (PRIOR ART)
FIG. 1B (PRIOR ART)
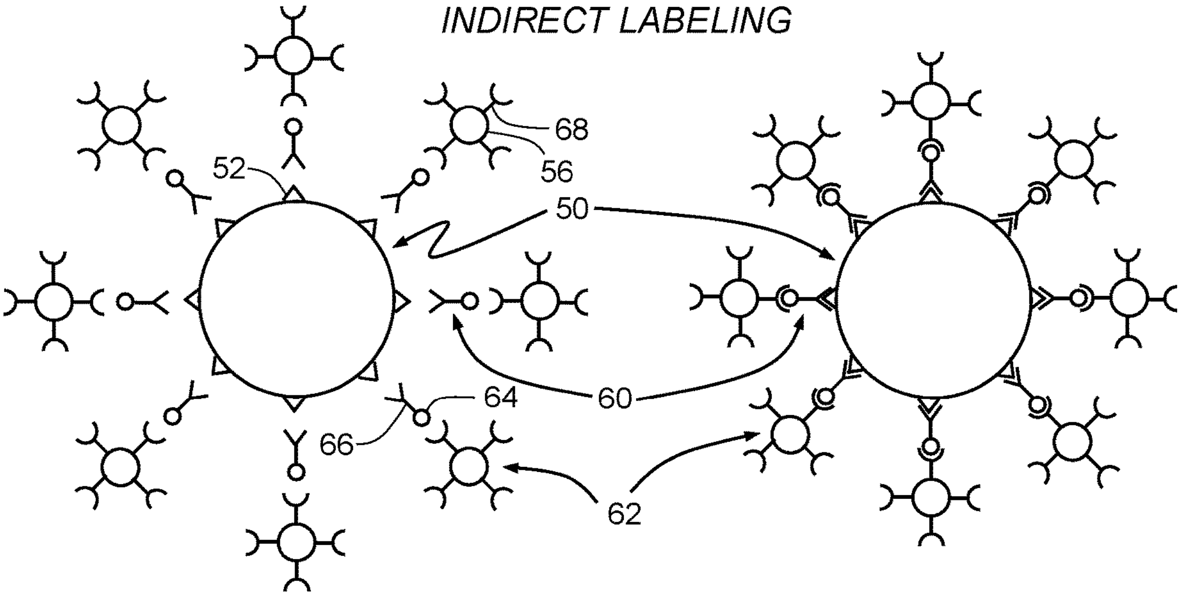
FIG. 2A (PRIOR ART)
FIG. 2B (PRIOR ART)

Conduit Disengaged from Magnetic Assembly

Conduit Engaging Magnetic Assembly

METHOD AND APPARATUS FOR MAGNETICALLY SORTING RARE CELLS

CROSS-REFERENCE TO RELATED APPLICATIONS

The present application is a continuation-in-part of application Ser. No. 18/144,447, filed on May 8, 2023, which is a continuation-in-part of application Ser. No. 18/111,486, filed on Feb. 17, 2023, which is a continuation-in-part of application Ser. No. 18/072,362, filed on Nov. 30, 2022, which claims priority to provisional application No. 63/406,437, filed on Sep. 14, 2022, and is a continuation-in-part of application Ser. No. 16/729,398, filed on Dec. 29, 2019, which is a continuation-in-part of application Ser. No. 15/911,115, filed on Mar. 3, 2018. All of these applications are incorporated herein by reference in their entirety, including their specifications.

BACKGROUND OF THE INVENTION

The present invention relates to separation and sorting of biological objects, and more particularly, to a method and apparatus for magnetically isolating rare cells.

The separation and sorting of biological objects or cells is critical to various biomedical applications, such as diagnostics and therapeutics. Biological objects may be sorted based on their respective physical properties, such as size and density, and biochemical properties, such as surface antigen expression.

In a biological object sorting process effectuated by an applied magnetic field, the biological object, such as a cell, which is typically nonmagnetic, can be magnetized for magnetic sorting purpose by attaching antibody-conjugated magnetic beads thereto, a process commonly known as magnetic labeling. FIG. 1A shows a cell 50 including a plurality of surface markers or antigens 52 on the cell surface thereof, and a plurality of antibody-conjugated magnetic beads 54 suspended in a fluid. Each of the antibody-conjugated magnetic beads 54 includes a magnetic entity 56 conjugated with one or more antibodies or other ligands 58, such as peptides and aptamers, that correspond to the surface markers 52. After an incubation period, the magnetic beads 54 may be directly attached to the cell 50 via the antigen-antibody interaction to form a magnetically labeled cell as shown in FIG. 1B, in a process known as direct labeling.

Alternatively, magnetic beads may be attached to a cell through an indirect labeling process. FIG. 2A shows a cell 50 including a plurality of surface markers or antigens 52 on the cell surface thereof, a plurality of intermediary links 60, and a plurality of magnetic beads 62 suspended in a fluid. Each of the intermediary links 60 includes one or more linking molecules 64, such as biotin or phycoerythrin (PE), conjugated to a primary antibody 66 that corresponds to the surface markers 52 of the cell 50. Each of the magnetic beads 62 includes a magnetic entity 56 conjugated with one or more secondary antibodies or ligands 68, such as streptavidin, that target the linking molecules 64. After an incubation period, the intermediary links 60 may attach to the cell 50 via the antigen-antibody interaction, and the magnetic beads 62 may further attach to the intermediary links 60 via PE-antibody, biotin-streptavidin, or other types of interactions, thereby forming a magnetically labeled cell as shown in FIG. 2B.

The magnetic beads 54 and 62 should ideally exhibit no magnetic moment in the absence of an applied magnetic field, thereby making the labeled cells indistinguishable from other biological objects in a cell suspension. As such, the magnetic entity 56 of the magnetic beads 54 and 62 normally consists of a magnetic nanoparticle or an aggregate of magnetic nanoparticles encapsulated in a nonmagnetic matrix because a magnetic particle may exhibit superparamagnetism as its size is reduced to tens of nanometers. In a sufficiently small ferromagnetic (e.g., iron) or ferrimagnetic (e.g., iron oxide) nanoparticle that exhibits superparamagnetism, magnetization can randomly flip direction under the influence of temperature. The typical time period between two such consecutive flips is known as the Neel relaxation time, or simply the relaxation time. Therefore, when the time period used to measure the magnetization of the magnetic nanoparticle is longer than the relaxation time thereof, the magnetic nanoparticle would appear to be nonmagnetic in the absence of an external magnetic field. During a cell sorting process, the magnetic nanoparticles of the magnetically labeled cells are first magnetized by sufficiently high magnetic field generated by a magnetic separator device and then attracted to regions of high magnetic field gradient.

After cells in fluid sample are magnetically labeled, they can be sorted or separated from the other non-labeled cells or biological objects in the fluid sample by a magnetic separator device. FIG. 3A shows a conventional magnetic separator device 70 comprising a container vessel 72 for holding static fluid sample 74 that contains the magnetically labeled cells 76 and a permanent magnet 78 placed in close proximity to a wall of the container vessel 72. The permanent magnet 78 generates a magnetic field in the container vessel 72 with the magnetic field gradient pointing towards the permanent magnet 78. After sufficient time, the magnetically labeled cells 76 will be gradually pulled by the force produced by the magnetic field towards the vessel wall and form an aggregate at the vessel wall, as shown in FIG. 3B. Because the magnetic field strength rapidly decreases as the distance from the permanent magnet 78 increases, the size of the vessel 72 and the fluid sample volume will be adversely limited.

FIG. 4 illustrates another conventional magnetic separator device 80 that separates magnetically labeled cells in static fluid sample contained in one or more wells 82. The magnetic device 80 uses multiple ferromagnetic poles 84, each of which has a trapezoidal tip, to act as a guide to concentrate the magnetic flux generated by multiple permanent magnets 86 attached thereto to increase the magnetic field strength and gradient near their tips. The corresponding magnetic field distribution, as delineated by magnetic field lines 88, shows that the magnetic field is strongest between the side surfaces of adjacent trapezoidal tips, as indicated by the small spacing between the field lines 88. By contrast, the magnetic field is much weaker above the pole tips, as indicated by the large spacing between the field lines 88. Accordingly, this necessitates the bottom portion of each well 82 to be disposed between the side surfaces of the pole tips, where the magnetic field is strong. The magnetically labeled cells in the conical-shaped wells 82 will be collected or condensed on or near the bottom of the wells 82 adjacent to the side surfaces of the trapezoidal tips of the ferromagnetic poles 84. Compared with the magnetic separator device 70 utilizing only the permanent magnet 78, the magnetic separator device 80 may improve the magnetic field strength and gradient by using the ferromagnetic poles 84 to concentrate the magnetic flux. Both devices 70 and 80, however, are designed to treat static fluid sample and thus may have limited throughput.

FIG. 5A illustrates a conventional magnetic separator device 90 that separates the magnetically labeled cells 76 as the fluid sample flows through the device 90. The device 90 includes a chamber 92 disposed between a pair of permanent magnets 94 that generate a magnetic field 96 across the chamber 92. The chamber 92 is filled with a column of porous aggregate of ferromagnetic or ferrimagnetic particles or spheres 98 that may be magnetized by the magnetic field 96 and produce relatively strong localized magnetic field and field gradient in small gaps between the particles or spheres 98, thereby magnetizing the magnetically labeled cells 76 and attracting them to the surface of the particles or spheres 98. Compared with the magnetic beads attached to the magnetically labeled cells 76, the ferromagnetic or ferrimagnetic particles or spheres 98 are much larger and may produce remanent magnetization after the permanent magnets 94 are removed from the chamber 92. The remanent magnetization may prevent or hinder the detachment of the magnetically labeled cells 76 from the surface of the particles or spheres 98 even after the removal of the magnetic field 96. While the magnetic separator device 90 may operate in a continuous flow manner and thus may potentially have a higher throughput than the magnetic separators 70 and 80 that operate in a static manner, the recovery of the magnetically labeled cells in certain applications (e.g., positive selection process where the magnetically labeled cells are the target cells) may be lower even with vigorous flushing of the chamber 92 using pressurized fluid to dislodge the magnetically labeled cells 76 from the surface of the particles or spheres 98, which may damage the same cells 76.

The column of porous aggregate of soft magnetic particles or spheres 98 in the chamber 92 may be replaced by one or more meshes 102 made of a ferromagnetic or ferrimagnetic material as shown in FIG. 5B. The magnetic separator device 100 may reduce the remanent magnetization encountered in the device 90 because the wires in the mesh 102 have smaller dimensions than the ferromagnetic or ferrimagnetic particles or spheres 98. However, the larger opening between adjacent wires in the mesh 102 may also weaken the localized magnetic field, thereby decreasing the device throughput. Both column-based devices 90 and 100 may introduced unwanted contaminants into the fluid sample as it flows through the ferromagnetic or ferrimagnetic material in the chamber 92.

FIG. 6 shows another magnetic separator device 104, which operates in a continuous flow manner without using a column of porous aggregate of ferromagnetic or ferrimagnetic material, thereby obviating the potential contamination and recovery issues associated therewith. The column-free device 104 includes a conduit 106 surrounded by a radial array of ferromagnetic poles 108 that conduct magnetic flux from a plurality of permanent magnets 110 and 112. Unlike the column-based magnetic separator devices 90 and 100, the fluid sample flows through the conduit 106 unimpeded along a direction perpendicular to the figure. The magnetic separator device 104 essentially rearranges the linear array of the ferromagnetic poles 84 of the static magnetic separator device 80 in a radial manner to create a magnetic periodic field at the center of the radially arranged ferromagnetic poles 108 and permanent magnets 110 and 112. Like the static device 80 shown in FIG. 4, the corresponding magnetic field distribution generated by the device 104, as delineated by magnetic field lines 114 between the trapezoidal tips of the ferromagnetic poles 108, shows that the magnetic field is strongest between the side surfaces of adjacent trapezoidal tips, as indicated by the small spacing between the field lines 114, and much weaker above the pole tips (i.e., inside the conduit 106), as indicated by the large spacing between the field lines 114. However, unlike the wells 82 that extend into the regions between the side surfaces of two adjacent trapezoidal tips, the conduit 106 of the magnetic separator device 104 does not extend into such regions, thereby making the magnetic field in the conduit 106 considerably weaker. This is further exacerbated by the limited time exposed to the magnetic field as the fluid sample flows through the conduit 106.

In an ideal magnetic labeling process, magnetic beads would attach themselves only to target cells, not the non-target cells. In practice, however, magnetic beads may attach themselves to a minute or trace amount of non-target cells directly or indirectly through intermediary links. The occurrence of such "non-specific binding" is normally low and may not markedly affect the final purity of the target cells if the frequency of the magnetically labeled target cells is significantly higher than that of the magnetically labeled non-target cells. However, for target cells that only have a miniscule presence in a heterogeneous mixture of cells (i.e., rare cells), the non-specific binding of magnetic beads to non-target cells will adversely reduce the final purity of the magnetically sorted sample. For example, hematopoietic stem cells (HSCs), with their unique self-renewal and differentiation capabilities, are present in the cord blood in a low frequency on the order of 1%. The frequency of hematopoietic progenitor cells (HPCs) in PBMC is on the order of 0.1%. Because of one or more of their limitations as discussed above, the aforementioned magnetic separator devices may not be suitable for separating or extracting rare cells that only have a miniscule presence in a heterogeneous mixture of cells.

For the foregoing reasons, there is a need for a method and apparatus for magnetically sorting biological objects that can efficiently extract and recover magnetically labeled rare cells with high purity and recovery rate from a suspension of heterogeneous mixture of cells.

SUMMARY OF THE INVENTION

The present invention is directed to a method that satisfies this need. A method having features of the present invention for magnetically sorting rare cells including the steps of providing a first fluid sample containing a first mixture of non-target and magnetically labeled target cells; flowing the first fluid sample unimpeded through a first conduit of a first magnetic separator device at a first flow rate to deposit a second mixture of non-target and magnetically labeled target cells having a higher purity of the magnetically labeled target cells than the first mixture of non-target and magnetically labeled target cells on a conduit wall of the first conduit; recovering the second mixture of non-target and magnetically labeled target cells deposited on the conduit wall of the first conduit by eluting with a buffer fluid to form a second fluid sample; flowing the second fluid sample unimpeded through a second conduit of a second magnetic separator device at a second flow rate to deposit a third mixture of non-target and magnetically labeled target cells having a higher purity of the magnetically labeled target cells than the second mixture of non-target and magnetically labeled target cells on a conduit wall of the second conduit; recovering the third mixture of non-target and magnetically labeled target cells deposited on the conduit wall of the second conduit by eluting with the buffer fluid to form a third fluid sample; flowing the third fluid sample unimpeded through a third conduit of a third magnetic separator device at a third flow rate to deposit a fourth mixture of non-target and magnetically labeled target cells having a higher purity of the magnetically labeled target cells than the third mixture of non-target and magnetically labeled target cells on a conduit wall of the third conduit; and recovering the fourth mixture of non-target and magnetically labeled target cells deposited on the conduit wall of the third conduit by eluting with the buffer fluid, wherein the second flow rate is greater than or equal to the first flow rate, the third flow rate is greater than or equal to the second flow rate and is greater than the first flow rate.

BRIEF DESCRIPTION OF DRAWINGS

These and other features, aspects, and advantages of the present invention will become better understood with regard to the following description, appended claims, and accompanying drawings where:

FIGS. 1A and 1B illustrate formation of a magnetically labeled cell by direct labeling process;

FIGS. 2A and 2B illustrate formation of a magnetically labeled cell by indirect labeling process;

For purposes of clarity and brevity, like elements and components will bear the same designations and numbering throughout the Figures, which are not necessarily drawn to scale.

DETAILED DESCRIPTION OF THE INVENTION

Figure 3A:
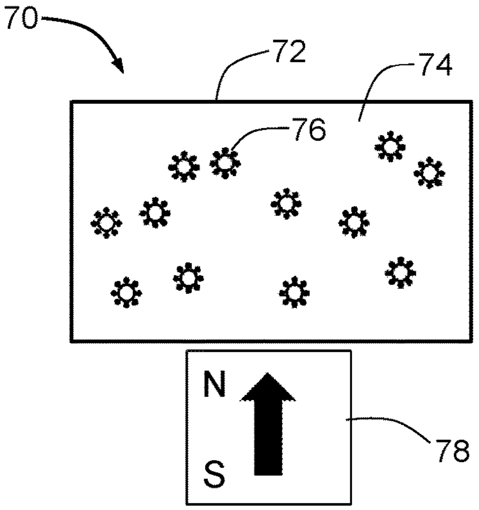
FIG. 3A (PRIOR ART)
FIGS. 3A and 3B illustrate sorting of magnetically labeled cells by a conventional static magnetic separator device.
Figure 3B:
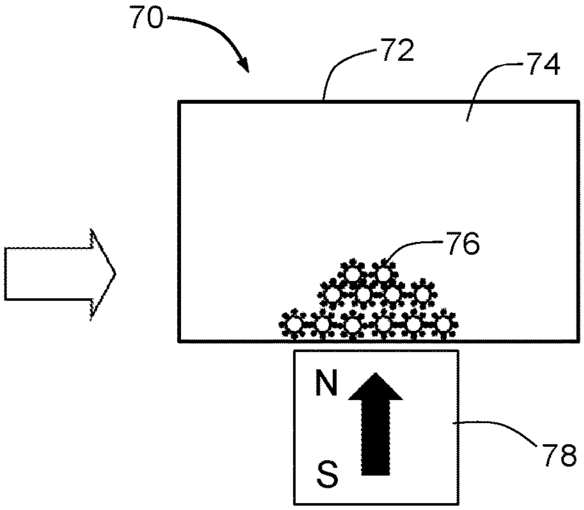
FIG. 3B (PRIOR ART)
Figure 4:
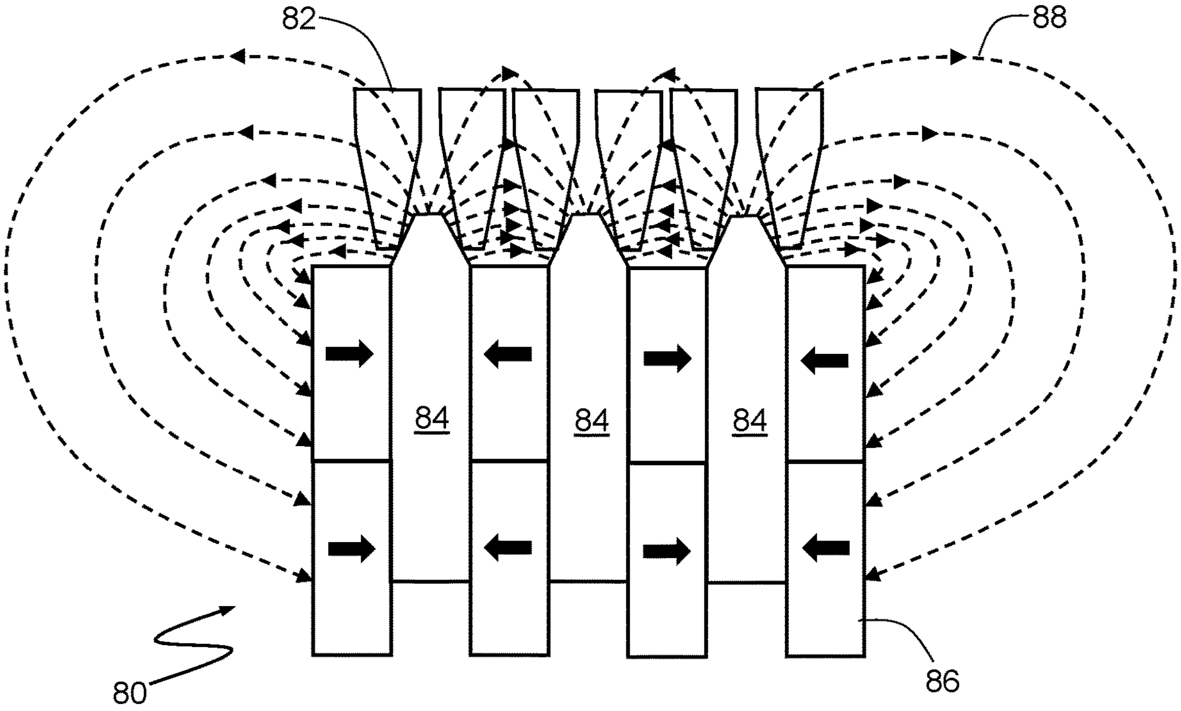
FIG. 4 (PRIOR ART)
FIG. 4 illustrates another conventional magnetic separator device for sorting magnetically labeled cells in static fluid sample.
Figure 5A:
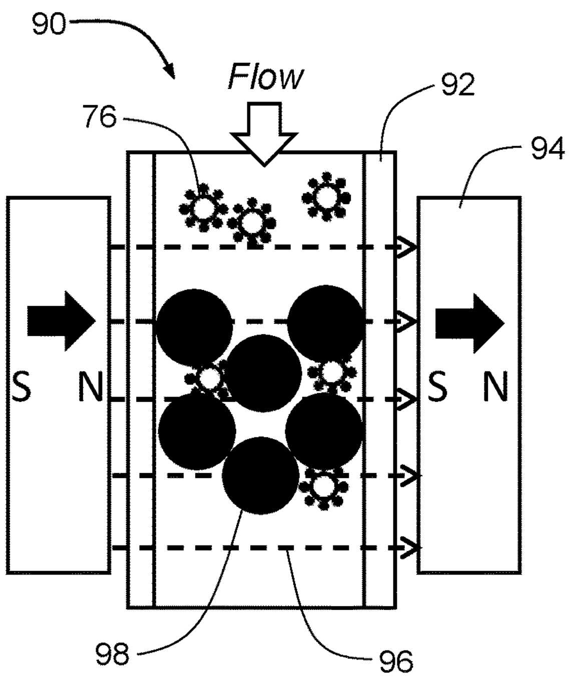
FIG. 5A (PRIOR ART)
FIGS. 5A and 5B illustrate two conventional magnetic separator devices that utilize a chamber filled with a column of porous aggregate of ferromagnetic or ferrimagnetic objects for sorting magnetically labeled cells flowing through the chamber.
Figure 5B:
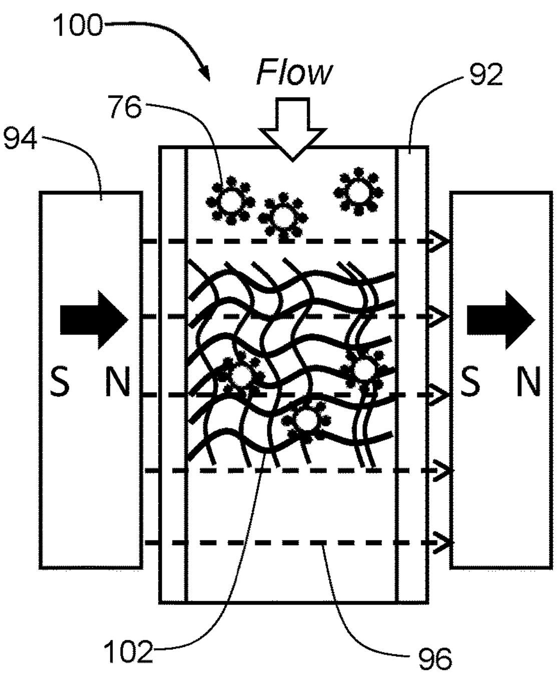
FIG. 5B (PRIOR ART)
Figure 6:
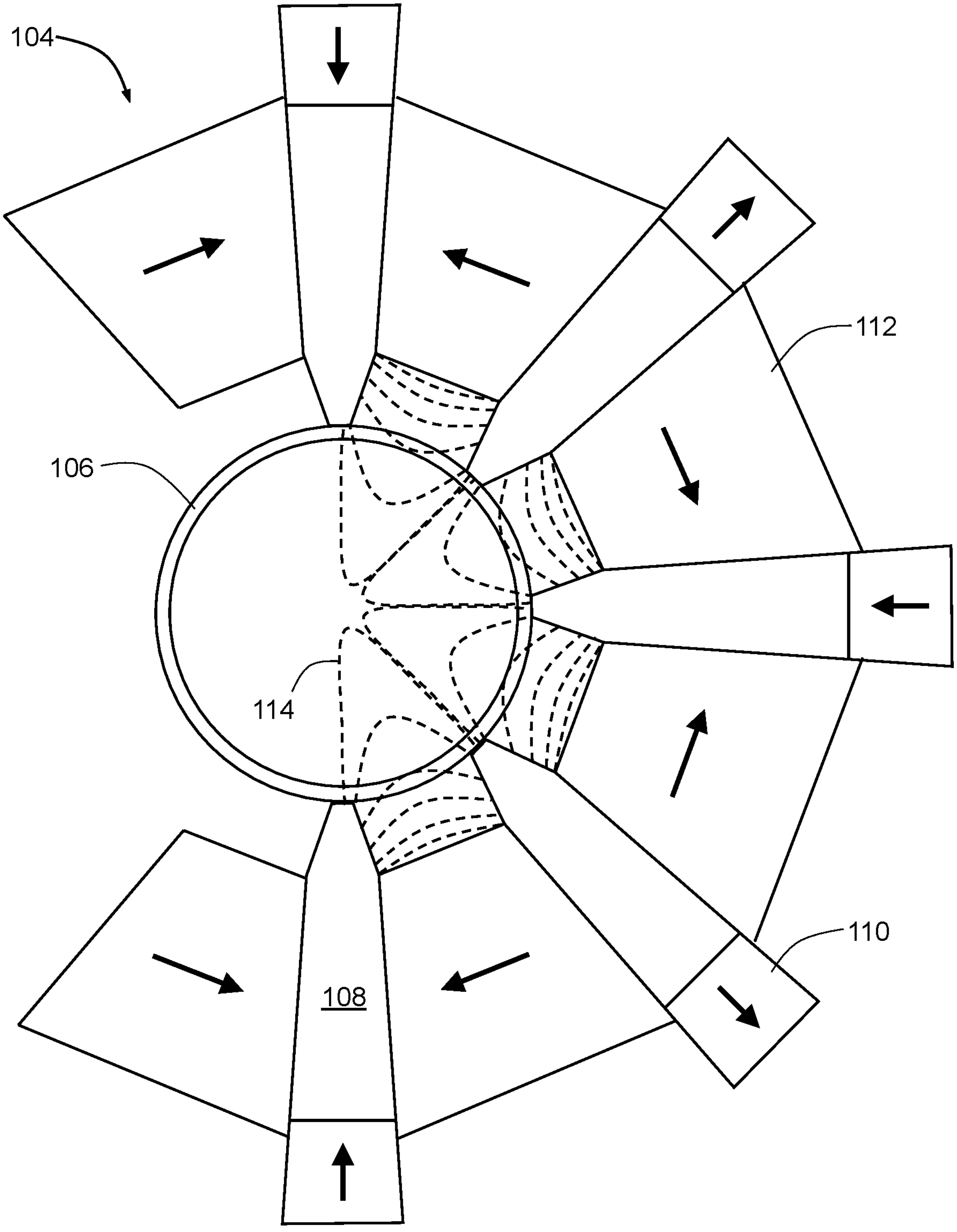
FIG. 6 (PRIOR ART)
FIG. 6 is a cross-sectional view corresponding to a column-free magnetic separator device for sorting magnetically labeled cells flowing through a conduit.

In the Summary above and in the Detailed Description, and the claims below, and in the accompanying drawings, reference is made to particular features (including method steps) of the invention. It is to be understood that the disclosure of the invention in this specification includes all possible combinations of such particular features. For example, where a particular feature is disclosed in the context of a particular aspect or embodiment of the invention, or a particular claim, that feature can also be used, to the extent possible, in combination with and/or in the context of other particular aspects and embodiments of the invention, and in the invention generally.

Where reference is made herein to a method comprising two or more defined steps, the defined steps can be carried out in any order or simultaneously, except where the context excludes that possibility, and the method can include one or more other steps which are carried out before any of the defined steps, between two of the defined steps, or after all the defined steps, except where the context excludes that possibility.

The term "biological objects" as used herein includes cells, bacteria, viruses, molecules, particles including RNA and DNA, cell cluster, bacteria cluster, molecule cluster, and particle cluster.

The term "biological sample" as used herein includes blood, body fluid, tissue extracted from any part of the body, bone marrow, hair, nail, bone, tooth, liquid and solid from bodily discharge, or surface swab from any part of body. "Fluid sample," or "sample fluid," or "liquid sample," or "sample solution" may include a biological sample in its original liquid form, biological objects being dissolved or dispersed in a buffer fluid, or a biological sample dissociated from its original non-liquid form and dispersed in a buffer fluid. A buffer fluid is a liquid into which biological objects may be dissolved or dispersed without introducing contaminants or unwanted biological objects. Biological objects and biological sample may be obtained from human or animal. Biological objects may also be obtained from plants and environment including air, water, and soil. A fluid sample may contain various types of magnetic or optical labels, or one or more chemical reagents that may be added during various process steps.

The term "sample flow rate" or "flow rate" is used herein to describe the volume amount of a fluid flowing through a cross section of a channel, a conduit, a fluidic part, a fluidic path, or a fluidic line in a unit time.

In the art of cell sorting and enrichment, the target population of biological objects is referred to as the "specific" objects of interest and those biological objects that are isolated, but are not desired, are termed "non-specific." The term "purity" describes the frequency of target or specific biological objects of interest and is quantified by the number of target biological objects divided by the total number of biological objects expressed in percentage. The term "recovery ratio" or "recovery rate" describes the sorting efficiency of biological objects and is quantified by the number of target biological objects recovered after sorting divided by the number of target biological objects present in the initial sample expressed in percentage.

The term "at least" followed by a number is used herein to denote the start of a range beginning with that number, which may be a range having an upper limit or no upper limit, depending on the variable being defined. For example, "at least 1" means 1 or more than 1. The term "at most"

followed by a number is used herein to denote the end of a range ending with that number, which may be a range having 1 or 0 as its lower limit, or a range having no lower limit, depending upon the variable being defined. For example, "at most 4" means 4 or less than 4, and "at most 40%" means 40% or less than 40%. When, in this specification, a range is given as "a first number to a second number" or "a first number-a second number," this means a range whose lower limit is the first number and whose upper limit is the second number. For example, "25 to 100 nm" means a range whose lower limit is 25 nm and whose upper limit is 100 nm.

Figure 7:
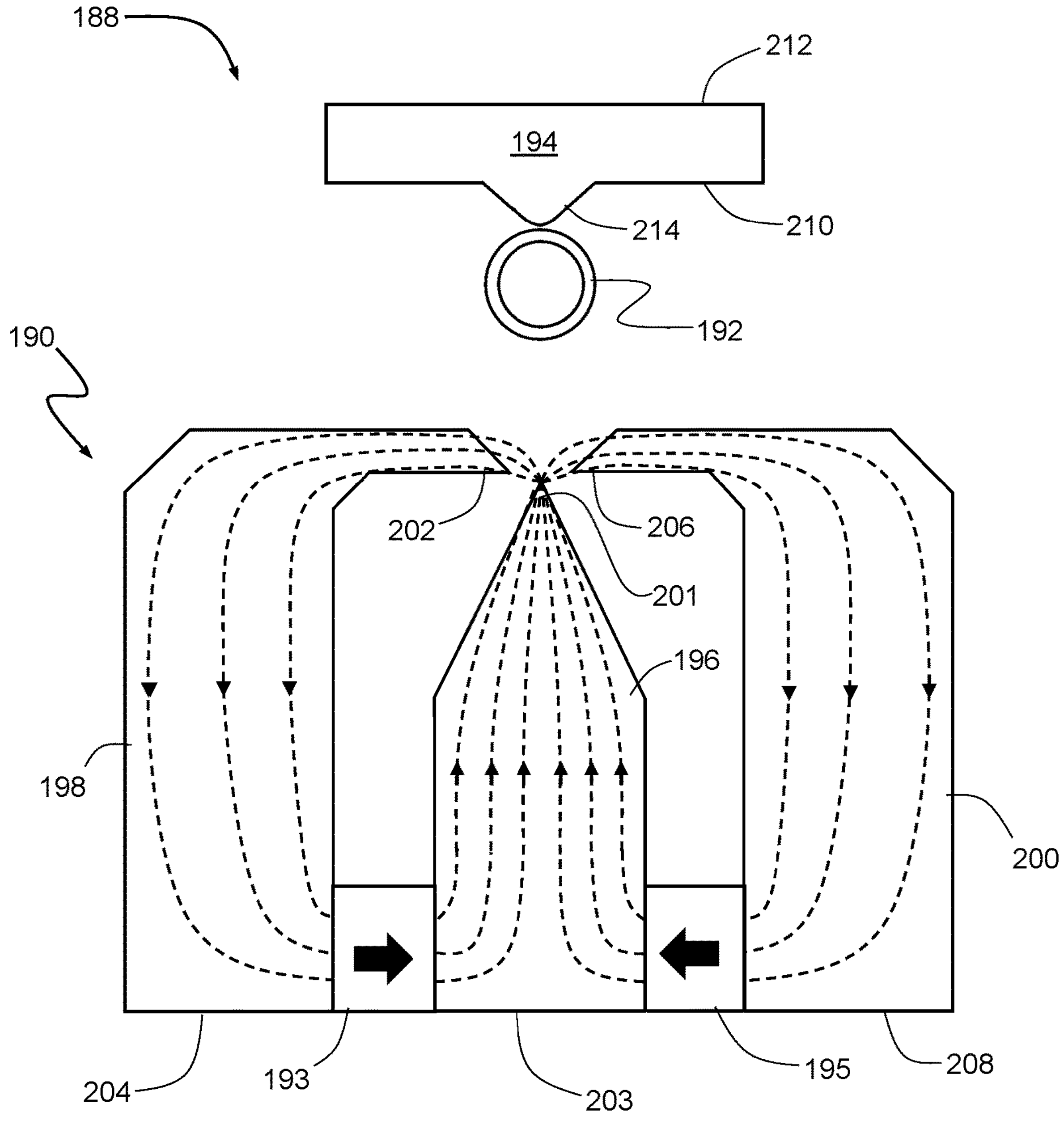
FIG. 7 is a cross-sectional view of an exemplary magnetic separator device when the holder and conduit are disengaged from the magnetic assembly.

FIG. 7 is a cross-sectional view of an exemplary magnetic separator device 188 that may be used to extract and recover magnetically labeled rare cells from a suspension of heterogeneous mixture of cells. The magnetic separator device 188 includes a magnetic assembly 190 for generating a magnetic field, a conduit 192 made of a pliable and/or flexible material for flowing a fluid sample for sorting, and a holder 194 for supporting the conduit 192. The figure shows the conduit 192 and the holder 194 being disengaged from the magnetic assembly 190. During the magnetic sorting process, however, the conduit 192 would be placed in close proximity to the magnetic assembly 190, thereby exposing the conduit 192 to the magnetic field generated by the magnetic assembly 190. Unlike the column-based magnetic separator devices 90 and 100, the fluid sample flowing through the conduit 192 along a direction perpendicular to the figure is unimpeded by a column of porous aggregate of magnetic objects.

The magnetic assembly 190 for generating the magnetic field to attract the magnetically labeled biological objects in the conduit 192 includes a magnetic flux source, which comprises first and second permanent magnets 193 and 195, a center magnetic flux guide 196 for conducting the magnetic flux from the magnetic flux source and forming a magnetic field, first and second side magnetic flux guides 198 and 200 disposed on opposite sides of the center magnetic flux guide 196 for conducting the magnetic flux from the magnetic flux source and forming the magnetic field at the gap between the flux guides 196-200.

The center magnetic flux guide 196 has a center tip 201 with a tapering shape and a center base 203 physically and/or magnetically coupled to the first and second permanent magnets 193 and 195 at their first pole (e.g., North pole). The center tip 201 may have a smaller cross section, which may be defined herein as the cross-sectional area perpendicular to the magnetic flux flow, than the center base 203, thereby concentrating the magnetic flux from the center base 203 to the center tip 201. The first side magnetic flux guide 198 has a first side tip 202 and a first side base 204 physically and/or magnetically coupled to the first permanent magnet 193 at its second pole (e.g., South pole). The first side tip 202 may have a smaller cross section than the first side base 204, thereby concentrating the magnetic flux from the first side base 204 to the first side tip 202. The second side magnetic flux guide 200 has a second side tip 206 and a second side base 208 physically and/or magnetically coupled to the second permanent magnet 195 at its second pole (e.g., South pole). The second side tip 206 may have a smaller cross section than the second side base 208, thereby concentrating the magnetic flux from the second side base 208 to the second side tip 206. Accordingly, each of the tips 201, 202, and 206 may have a higher magnetic flux density than the corresponding base 203, 204, or 208. The first and second side magnetic flux guides 198 and 200 may be parallel at their bases 204 and 208 and bending or kinking inward toward the center tip 201 at their tips 202 and 206, which may be pointed at each other. The ends of the first and second side tips 202 and 206 may each have a chisel edge profile with the bevel side facing upward or outward away from the center magnetic flux guide 196. The center tip 201 may be positioned below the first and second side tips 202 and 206. The conduit 192 may be operably nestled in the gap or concave space delineated by the tip end of the center tip 201 and the bevels of the first and second side tips 202 and 206 during the magnetic sorting process, thereby exposing the conduit 192 to the magnetic field generated by the magnetic assembly 190.

The first permanent magnet 193 may be disposed between the center base 203 and the first side base 204, and the second permanent magnet 195 may be disposed between the center base 203 and the second side base 208. The first and second permanent magnets 193 and 195 have opposite magnetization directions that may be oriented substantially perpendicular to the center magnetic flux guide 196.

The center base 203 is magnetically coupled to the first and second permanent magnets 193 and 195 at their first pole (e.g., North pole), while the first and second side bases 204 and 208 are magnetically coupled to the first and second permanent magnets 193 and 195 at their second pole (e.g., South pole), respectively, thereby rendering the first and second side tips 202 and 206 (second polarity) and the center tip 201 (first polarity) to have opposite magnetic polarities and forming a strong magnetic field at or near the gaps between the tips 201, 202, and 206 to deposit the magnetically labeled biological objects on the conduit wall.

With continuing reference to FIG. 7, the holder 194 may have a first surface 210 facing the conduit 192 and a second surface 212 opposite the first surface 210. The first surface 210 may have a ridge structure 214 protruded from the first surface 210 that functions as a mechanical press for pushing the conduit 192 into the gap or concave space delineated by the tip end of the center tip 201 and the bevels of the first and second side tips 202 and 206 during the magnetic sorting process. Additionally, the ridge structure 214 of the holder 194 may be made of a magnetic material that conducts magnetic flux like a "floating" or top magnetic flux guide. In addition to acting like a mechanical press for pushing the conduit 192 against the tips 201, 202, and 206, the ridge structure 214 made of the magnetic material may magnetically interact with the tips 201, 202, and 206 to further enhance the magnetic field therebetween, thereby increasing the magnetic sorting efficiency.

Figure 8:
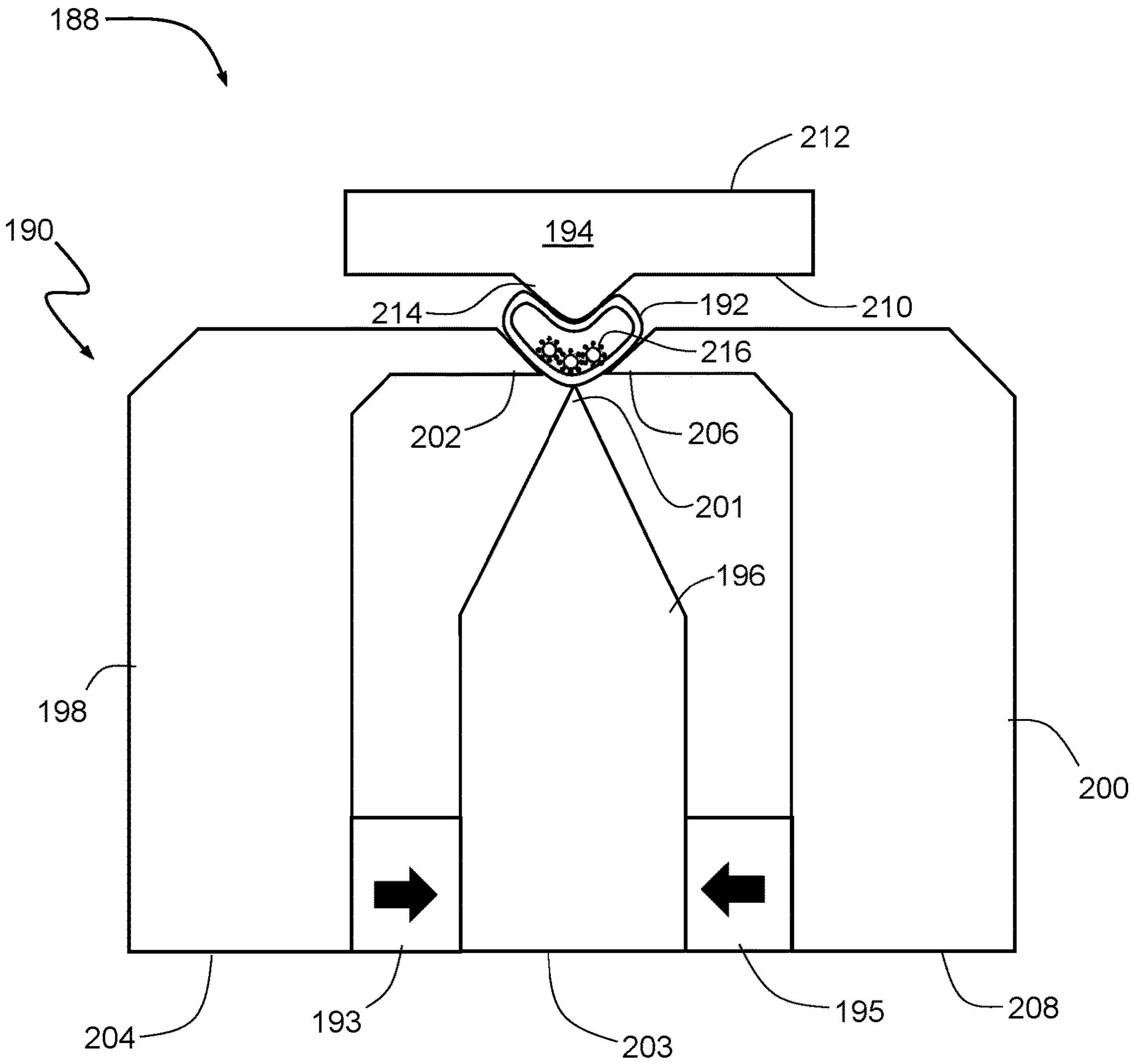
FIG. 8 is a cross-sectional view of the magnetic separator device of FIG. 7 when the conduit is squeezed against the tips of the magnetic assembly by the holder during the magnetic sorting process.

FIG. 8 is a cross-sectional view of the magnetic separator device 188 when the conduit 192 is squeezed between the ridge structure 214 of the holder 194 and the tip ends 201, 202, and 206 of the three magnetic flux guides 196-200 during the magnetic sorting process. The holder 194 may push the deformed or distorted conduit 192 further into the gap between the center tip 201 and the first side tip 202 and the gap between the center tip 201 and the second side tip 206, where the magnetic field may be the strongest. Pushing the conduit 192 against the tip end of the center tip 201 and the bevels of the first and second side tips 202 and 206 may expose more fluid sample flowing through the conduit 192 to stronger magnetic field. During the magnetic sorting process, the magnetically labeled biological objects 216 may be deposited on the bottom of the conduit 192 near the center tip 201, where the magnetic field gradient may be highest.

In the embodiment where the ridge structure 214 is made of a soft magnetic material, the ridge structure 214 may act like a top magnetic flux guide when positioned in close proximity to the tips 201, 202, and 206 during the magnetic sorting process. The magnetic ridge structure 214 may conduct flux from the first and second side magnetic flux guides 198 and 200 and thus may have the same magnetic polarity (second polarity) as the first and second side tips 202 and 206, thereby further enhancing the magnetic field between the ridge structure 214 and the center tip 201.

Other column-free magnetic separator devices, such as those disclosed in U.S. application Ser. No. 18/072,362, which is incorporated herein by reference, may also be employed to deposit magnetically labeled biological objects on the conduit wall during the magnetic sorting process.

The magnetic flux guides 196-200 each may be made of a soft magnetic material or a material with relatively high magnetic permeability that comprises any one of iron (Fe), cobalt (Co), nickel (Ni), or any combination thereof. For example and without limitation, any of the magnetic flux guides 196-200 may be made of iron. The conduit 192 may be made of any suitable flexible and/or pliable material that may be bent or deformed, such as but not limited to rubber, plastics, or any suitable polymeric material. The holder 194 may be made of any suitable nonmagnetic material, such as but not limited to aluminum, glass, a nonferrous metal or alloy, plastics, or any suitable polymeric material. In some embodiments, the ridge structure 214 of the holder 194 that comes into contact with the conduit 192 may be made of a soft magnetic material, such as but not limited to any of the soft magnetic materials described above for the magnetic flux guides 196-200.

Figure 9:
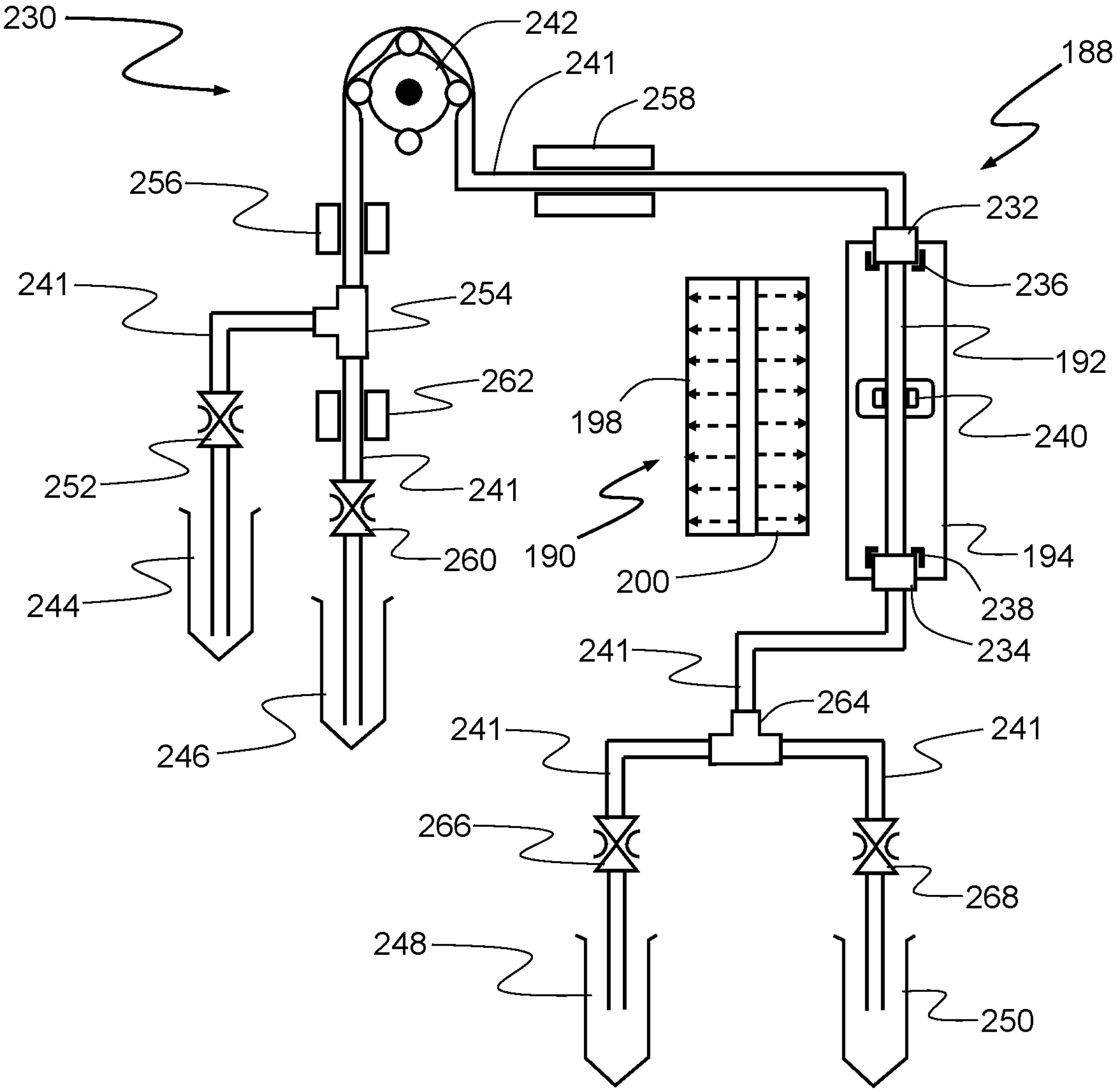
FIG. 9 is a schematic diagram depicting an exemplary fluidic circuit including the magnetic separator device when the holder and conduit are disengaged from the magnetic assembly.

FIG. 9 is a schematic diagram depicting an exemplary fluidic circuit 230 that includes the magnetic separator device 188 when the holder 194 and conduit 192 are disengaged from the magnetic assembly 190. The conduit 192 may include two collars 232 and 234 attached thereto and may be reversibly fastened to or suspended on the holder 194 by snapping the collars 232 and 234 onto a pair of supports or brackets 236 and 238 at two ends of the holder 194. The conduit 192 may be stretched and suspended in between the brackets 236 and 238 when fastened to the holder 194, thereby ensuring that the flexible conduit 192 remains straight and aligns to the gap formed between the tips 201, 202, and 206 of the magnetic flux guides 196-200 when engaging the magnetic assembly 190 during the magnetic sorting process. The holder 194 may additionally contain an opening or hole, through which an agitator arm with a fork end 240 clutching the conduit 192 may apply a transverse vibration to the conduit 192 to loosen magnetically labeled biological objects deposited on the conduit wall.

With continuing reference to FIG. 9, the conduit 192 may be a part of a network of fluidic lines 241 that uses a peristaltic pump 242 to draw fluid from a wash or buffer fluid container 244 and a fluid sample container 246 and discharge fluid to a positive collection container 248 and a negative collection container 250. Under the peristalsis effect of the peristaltic pump 242, fluid in the buffer fluid container 244 can reach the conduit 192 of the magnetic separator device 188 by passing through a first pinch valve 252, a first three-way flow connector 254, a first air detector 256, the peristaltic pump 242, and a blockage sensor 258. Similarly, fluid in the fluid sample container 246 can reach the conduit 192 of the magnetic separator device 188 by passing through a second pinch valve 260, a second air detector 262, the first three-way flow connector 254, the first air detector 256, the peristaltic pump 242, and the blockage sensor 258. Fluid discharged from the conduit 192 of the magnetic separator device 188 can be collected at the positive collection container 248, by passing through a second three-way flow connector 264 and a third pinch valve 266, and/or collected at the negative collection container 250, by passing through the second three-way flow connector 264 and a fourth pinch valve 268.

The network of fluidic lines 241 in the fluidic circuit 230 may be made of any suitable flexible and/or pliable material that may be bent or deformed, such as but not limited to rubber, plastics, or any suitable polymeric material. In an embodiment, the network of fluidic lines 241 and the conduit 192 are made of the same flexible and/or pliable material. The network of fluidic lines 241, including the conduit 192, may be constructed, interconnected, and supplied as a disposable tubing set. Additional connectors or different types of connectors or fittings may also be used to construct the network of fluidic lines 241 in the fluidic circuit 230.

The first and second pinch valves 252 and 260 may be used to regulate the flow of fluid from/to the buffer fluid container 244 and the fluid sample container 246, respectively. The third and fourth pinch valves 266 and 268 may be used to regulate the flow of fluid to the positive and negative collection containers 248 and 250, respectively. The pinch valves 252, 260, 266, and 268 close the flow of fluid in the fluidic lines 241 by squeezing the walls of a flexible fluidic line against one another. The first and second air detectors 256 and 262, which use ultrasound to sense air bubbles or air gaps in the fluidic lines 241 before the peristaltic pump 242, may detect leaks in the fluidic lines 241 or depletion of the buffer fluid and fluid sample in the buffer fluid container 244 and the fluid sample container 246, respectively. The blockage sensor 258, which is disposed along the fluidic line between the peristaltic pump 242 and the magnetic separator device 188, uses capacitive sensing to detect the blockage of flow through the magnetic separator device 188 and beyond. The operation of the electromechanical components 242, 252, 256-262, 266, and 268 may be controlled by a central process unit (CPU) or computer (not shown).

In the embodiment shown in FIG. 9, the peristaltic pump 242, the pinch valves 252, 260, 266, and 268, the air sensors 256 and 262, and the blockage sensor 258 are external to the flexible fluidic lines 241 of the fluidic circuit 230, thereby preventing direct contact between the fluid in the fluidic lines 241 and these components 242, 252, 256-262, 266, and 268. However, it should be understood that the fluidic circuit 230 may alternatively be constructed using other types of pumps, sensors, valves, or fluidic lines. For example, a portion of the network of fluidic lines 241 may be made of a rigid material, which may require the use of other types of pump and valves that are positioned in the fluid pathways and thus come into direct contact with the fluid flowing through the rigid fluidic lines.

Operation of the fluidic circuit 230 for magnetic sorting will now be described with reference to the schematic diagram of FIG. 10, which shows the conduit 192 engaging the magnetic assembly 190. The holder 194, which presses the conduit 192 against the magnetic assembly 190 during the magnetic sorting process (as shown in FIG. 8), is omitted in FIG. 10 for reasons of clarity. An exemplary process of magnetic sorting begins by providing a fluid sample including a mixture of magnetically labeled and unlabeled biological objects in the fluid sample container 246. The fluid sample is pumped by the peristaltic pump 242 into the conduit 192 engaging the magnetic assembly 190, with the first and third pinch valves 252 and 266 shut and the second and fourth pinch valves 260 and 268 opened. As the fluid sample flows through the conduit 192 that is exposed to the magnetic field generated by the magnetic assembly 190, ideally, the magnetically labeled biological objects are attracted by the magnetic field and are deposited or collected on the conduit wall, while the nonmagnetic or unlabeled biological objects in the depleted fluid sample are flushed into the negative collection container 250.

After the separation of the magnetically labeled biological objects deposited on the conduit wall of the magnetic separator device 188 from the unlabeled biological objects in the negative collection container 250 is completed, the process of recovering the magnetically labeled biological objects proceeds by moving the holder 194 and the conduit 192 away from the magnetic assembly 190 and the magnetic field generated thereby, as shown in FIG. 9. However, simply removing the conduit 192 from the magnetic field and flushing the conduit 192 with buffer fluid may not cause the accumulation or buildup of magnetically labeled biological objects on the conduit wall to dislodge from the conduit wall and/or dissociate into individual biological objects for recovery, because the magnetic beads on a biological object may still experience magneto-static field from neighboring magnetic beads and/or magnetic beads of neighboring biological objects. Therefore, mechanical agitation may be applied to the conduit 192 by the agitator arm 240, which has one end attached to a vibration source and another end (i.e., fork end) clutching the conduit 192, to loosen the magnetically labeled biological objects deposited on the conduit wall in the presence of a static or moving fluid.

With continuing reference to FIG. 9, during the recovery process, a buffer fluid in the buffer fluid container 244 is pumped into the conduit 192 by the peristaltic pump 242, with the second and fourth pinch valves 260 and 268 shut and the first and third pinch valves 252 and 266 opened. As the buffer fluid flows through the conduit 192, the agitator arm 240 may impart transverse vibration to the conduit 192 to loosen and dissociate the accumulation or buildup of magnetically labeled biological objects on the conduit wall. The buffer fluid carrying the magnetically labeled biological objects then flows from the conduit 192 into the positive collection container 248. Alternatively, the recovery of the magnetically labeled biological objects from the conduit wall may be carried out by imparting the transverse vibration to the conduit 192 while the flow of the buffer fluid is temporarily stopped when the conduit 192 is filled with the buffer fluid. The application of the transverse vibration under the static fluid condition may reduce the amount of buffer fluid required for the recovery process. After the elution of the magnetically labeled biological objects deposited on the conduit wall with the buffer fluid, additional buffer fluid may be added to dilute the fluid sample in the positive collection container 248 and resuspend the magnetically labeled biological objects for subsequent process. Alternatively, the elution of the magnetically labeled biological objects may be carried out by using excess buffer fluid to dilute the fluid sample without the separate dilution step.

The operation of the fluidic circuit 230 for magnetic sorting as described above may be automated by a computer program executed by a CPU or computer.

Figure 10:
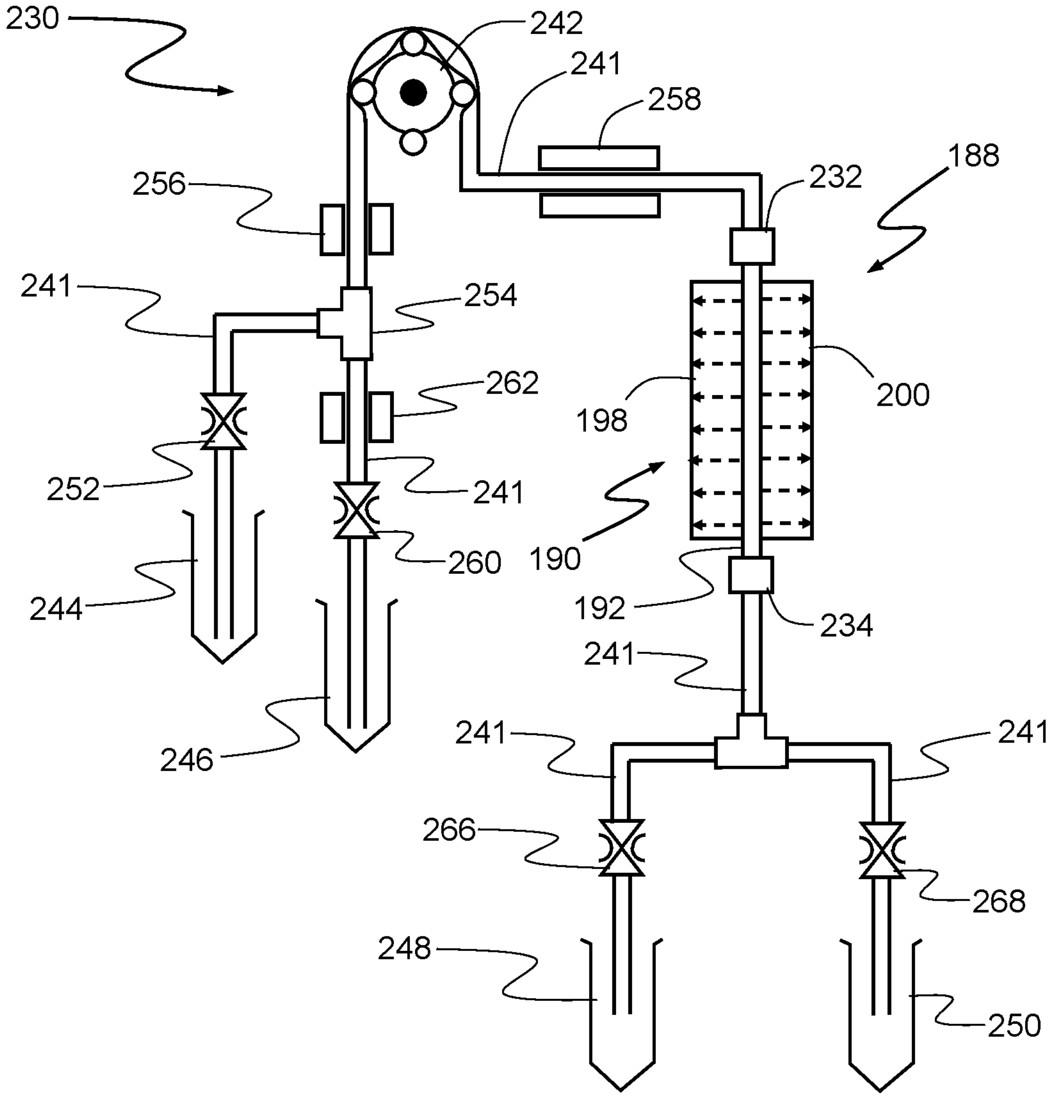
FIG. 10 is a schematic diagram depicting the fluidic circuit including the magnetic separator device when the conduit is pushed against the tips of the magnetic assembly during the magnetic sorting process.
Figure 11:
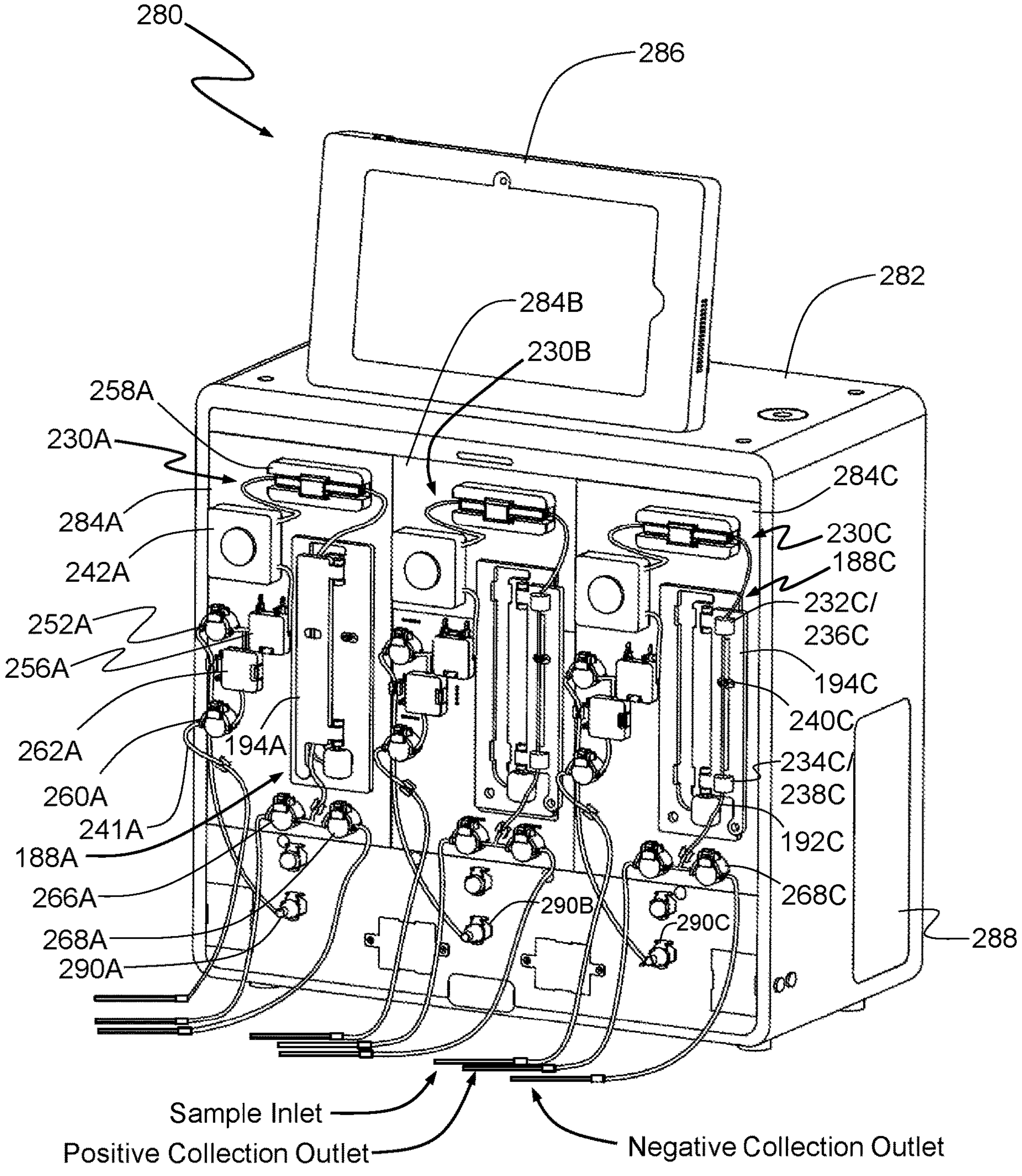
FIG. 11 is a perspective view of an automated magnetic separator system that includes multiple fluidic circuits that can independently perform magnetic sorting.

The fluidic circuit 230 including the magnetic separator device 188, as shown in FIGS. 9 and 10, may be implemented as part of a magnetic separator system 280 shown in a perspective view in FIG. 11. The magnetic separator system 280 includes a system housing 282, first, second, third magnetic separator modules 284A-284C residing in the housing 282, and an external computer 286 for controlling the electrical and electromechanical components in the system 280. The three magnetic separator modules 284A-284C may be substantially identical. A rack for holding the containers 246-250, which is normally disposed in front of the system housing 282 and the modules 284A-284C, and the containers 246-250 are omitted in the drawing in order to present an unobstructive view of the modules 284A-284C.

Each of the first, second, and third magnetic separator modules 284A-284C includes a corresponding fluidic circuit 230A, 230B, or 230C. In the configuration shown, all three fluidic circuits 230A-230C draw a wash or buffer fluid from a common container or tank (not shown) disposed inside the system housing 282. The common container can be access through a side panel door 288 and the wash or buffer fluid stored in the common container can be extracted through three inlet ports 290A-290C disposed on the front of the system housing 282.

Each of the first, second, and third fluidic circuits 230A-230C includes a network of fluidic lines and fluidic components analogous to those of the fluidic circuit 230 shown in FIGS. 9 and 10. For example and without limitation, the first fluidic circuit 230A includes a network of fluidic lines 241A, first and second pinch valves 252A and 260A for regulating the flow of fluid from/to the first inlet port 290A and the sample inlet, respectively; and third and fourth pinch valves 266A and 268A for regulating the flow of fluid to the positive and negative collection outlets, respectively; a magnetic separator device 188A; a peristaltic pump 242A for moving fluid from the inlets of the network of fluidic lines 241A, through the magnetic separator device 188A, to the collection outlets of the network of fluidic lines 241A; first and second air detectors 256A and 262A for sensing air bubbles or air gaps in the fluidic lines 241A before the peristaltic pump 242A; and a blockage sensor 258A disposed between the peristaltic pump 242A and the magnetic separator device 188A for detecting the blockage of flow through the magnetic separator device 188A and beyond. The second and third fluidic circuits 230B and 230C are substantially identical to the first fluidic circuit 230A and have the same fluidic components. However, not all fluidic components of the second and third fluidic circuits 230B and 230C are explicitly labeled in FIG. 11 for reasons of legibility of the drawing.

Each of the magnetic separator modules 284A-284C may further include various electrical components (not shown) connected to assorted electrical components and a power supply in the system housing 282. The computer 286, which is connected to the system housing 282, may control the electrical and electromechanical components in the system 280 to allow individual magnetic separator modules 284A-284C to operate independently. For example and without limitation, in the configuration shown in FIG. 11, the holder 194A of the first magnetic separator module 284A clamps the flexible conduit against the magnetic assembly (analogous to FIG. 8), while the holder 194C of the third magnetic separator module 284C and the conduit 192C move away from the magnetic assembly with the conduit 192C engaging the agitator arm 240C through an opening or hole in the holder 194C (analogous to FIG. 9). The magnetic sorting process may also be automated by the computer 286.

In a column-free continuous flow magnetic separator device, such as but not limited to the magnetic separator device 188 shown in FIGS. 7-10, there may be at least two competing forces in the deposition of magnetically labeled biological objects on the conduit wall. One is the magnetic attraction force resulting from the interaction between the magnetic beads attached to biological objects and the magnetic field generated by the magnetic assembly. The other one is the hydrodynamic force resulting from the sample flow that carries the biological objects along. The magnetic attraction force tends to attract the magnetically labeled biological objects to the conduit wall, while the hydrodynamic force tends to carry the magnetically labeled biological objects away from the conduit wall or hinder the deposition of the magnetically labeled biological objects on the conduit wall. Therefore, it is generally accepted that for a given continuous flow magnetic separator device, the purity of the magnetically sorted sample can be improved by decreasing the sample flow rate, which reduces the hydrodynamic force and effectively increases the magnetic attraction by exposing the magnetically labeled biological objects to the magnetic field for a longer period of time.

However, the inventors have discovered that reduction of sample flow rate did not necessarily improve the final purity when magnetically sorting rare cells, such as circulating tumor cells (CTCs) from whole blood, because of the presence of magnetically labeled non-target cells, such as granulocytes, caused by non-specific binding. It was also observed that the magnetically labeled non-target cells had fewer magnetic beads attached thereto compared with the magnetically labeled target cells. This implies that the magnetically labeled non-target cells deposited on the conduit wall are held by weaker magnetic attraction force and may be selectively removed by increasing the hydrodynamic force, as long as the magnetic separator device can generate sufficiently high magnetic field and field gradient to substantially retain the magnetically labeled target cells on the conduit wall under the increased hydrodynamic force condition.

The miniscule presence of rare cells in a typical fluid sample that contains a heterogeneous mixture of cells and biological objects means that unwanted cells or biological objects may account for 99% or more of all cells or biological objects in the fluid sample. Therefore, multiple passes through the magnetic separator device may be required to attain a final purity for the rare cells of at least 40%, preferably at least 70%, more preferably at least 80%, and most preferably at least 90%. The first iteration through the magnetic separator device may remove a great majority of the unlabeled cells or biological objects while retaining as much as possible the magnetically labeled cells, which may include both the target and non-target cells. After a great majority of the unlabeled cells and/or biological objects is removed, the magnetically labeled non-target cells and other remaining unlabeled cells and/or biological objects that deposit on the conduit wall may be selectively removed by increasing the hydrodynamic force in subsequent pass(es) through the magnetic separator device, thereby increasing the purity of the magnetically labeled target cells in the final sample.

According to an embodiment of the present invention as applied to a method for magnetically sorting rare cells, the sorting process begins by providing a column-free continuous flow magnetic separator device that can generate sufficiently high magnetic field and field gradient, such as but not limited to the magnetic separator device 188 shown and described above, and a first fluid sample containing a population of magnetically labeled rare cells as target cells in a suspension of heterogeneous mixture of cells. The frequency of the magnetically labeled rare cells in the first fluid sample, as determined by cytometry or other suitable cell counting methods, is preferably at most 5%, more preferably at most 1%, and most preferably at most 0.1%. Examples of rare cells include, but not limited to, hematopoietic stem cells (HSCs) in cord blood, HSCs in bone marrow, plasma cells in bone marrow, hematopoietic progenitor cells (HPCs) in peripheral blood, and CTCs in peripheral blood. These rare cells have CD34, CD138, EpCAM, or other uniquely identifiable antigen expressions and therefore can be magnetically labeled with magnetic beads accordingly.

The preparation process for the first fluid sample for magnetic sorting, which contains a first mixture of non-target cells and magnetically labeled target cells (e.g., rare cells), may begin by adding a magnetic reagent to an initial raw sample (e.g., mononuclear cells) for directly labeling the rare cells with magnetic beads. Alternatively, the rare cells may be indirectly labeled by first adding a reagent containing intermediate links, such as phycoerythrin (PE) conjugated with the targeted antibody, to the initial raw sample, thereby attaching the intermediate links to the rare cells after an incubation period. A magnetic reagent containing magnetic beads that target the intermediate links may then be added to the mixture of initial raw sample and the reagent containing intermediate links to complete the indirect magnetic labeling process after another incubation period. A first buffer fluid may be added to the fluid sample containing the rare cells before or after the magnetic labeling process to adjust the concentration of the cells in the first fluid sample and/or the viscosity of the first fluid sample. The dilution of the initial raw sample with the first buffer fluid may reduce coalescence and clumping of cells and/or reduce potential obstruction by unlabeled cells as magnetically labeled cells move toward conduit wall under the influence of the external magnetic field exerted by the magnetic separator device, thereby facilitating the sorting process.

The process continues by flowing a first volume of the first fluid sample, which contains the first mixture of non-target cells and magnetically labeled target cells (e.g., rare cells), through the conduit (e.g., 192) of the magnetic separator device (e.g., 188) at a first flow rate to deposit a second mixture of non-target cells and magnetically labeled target cells on the conduit wall, while a great majority portion, preferably at least 90%, more preferably at least 95%, of the non-target cells exits the magnetic separator device 188 with the depleted first fluid sample. Therefore, the second mixture of cells has a higher purity of magnetically labeled target cells than the first mixture of cells. Using the fluidic circuit 230 of FIG. 10 as an example, the first fluid sample may flow from the fluid sample container 246 to the magnetic separator device 188 and the depleted first fluid sample may flow from the magnetic separator device 188 to the negative collection container 250 during the first sorting process.

The accumulated second mixture of cells on the conduit wall may include magnetically labeled target cells (e.g., rare cells) and magnetically labeled and unlabeled non-target cells, because the initial passage of the first fluid sample through the magnetic separator device is intended to remove a great majority but not all of the non-target cells while retaining as much as possible the magnetically labeled target cells. This may be achieved by controlling the first flow rate, which directly influence the hydrodynamic force that counters the magnetic attraction force on the magnetically labeled cells. For example, a higher first flow rate may be used for a magnetic separator that generates higher field gradient, and/or target cells having higher density of targeted antigen, and/or larger magnetic beads without decreasing the recovery rate of the magnetically labeled target cells. Therefore, the first flow rate of the first fluid sample may be adjusted such that the recovery rate of the magnetically labeled target cells is at least 50%, preferably at least 60%, more preferably at least 70%, and most preferably at least 80%.

After passage of the first fluid sample through the magnetic separator device 188, the second mixture of non-target cells and magnetically labeled target cells deposited on the conduit wall is recovered by elution with a second buffer fluid, thereby forming a second fluid sample. Prior to flowing the second fluid sample through the magnetic separator device, the recovered second mixture of cells in the second fluid sample may be further diluted and resuspended with additional second buffer fluid. Alternatively, the elution process may be carried out by using an excess of the second buffer fluid to dilute the recovered second mixture of cells without the separate dilution step. The second buffer fluid may be same as the first buffer fluid.

The recovery/elution process may be carried out by using the magnetic separator device 230 in the recovery position as shown in FIG. 9. The second buffer fluid may flow from the buffer fluid container 244 through the conduit 192 of the magnetic separator device 188 to flush the second mixture of cells accumulated on the conduit wall to the positive collection container 248. During the elution process, the agitator arm 240 that clutches the conduit 192 may provide transverse vibration to the conduit 192 to dissociate and loosen the second mixture of cells from the conduit wall. The dilution/resuspension process may be similarly carried out like the recovery/elution process described above, except with higher volume of the second buffer fluid and without application of transverse vibration to the conduit 192.

The second fluid sample having a second volume, which includes the second mixture of non-target cells and magnetically labeled target cells, the second buffer fluid used for elution, and additional second buffer fluid as dilutant, if any, is flowed through the conduit (e.g., 192) of the magnetic separator device (e.g., 188) for the second time at a second flow rate to deposit a third mixture of non-target cells and magnetically labeled target cells on the conduit wall that has a higher purity of the magnetically labeled target cells than the second mixture of cells. The second volume may be higher than the first volume of the first fluid sample by 10-150%, preferably 20-120%, more preferably 30-90%, and most preferably 40-70%. Therefore, the second fluid sample may have a significantly lower concentration of cells and/or biological objects than the first fluid sample owing to larger volume while containing fewer cells and/or biological objects.

Using the fluidic circuit 230 of FIG. 10 as an example, the second fluid sample may flow from the fluid sample container 246 to the magnetic separator device 188 and the depleted second fluid sample may flow from the magnetic separator device 188 to the negative collection container 250 during the sorting process. The second flow rate may be same as or higher than the first flow rate to facilitate the further separation of the magnetically labeled target cells from the non-target cells in the second fluid sample. The ratio of the second flow rate to the first flow rate may be 100-300%, preferably 120-250%, and more preferably 140-200%. The use of a higher second flow rate, as compared to the first flow rate, may further increase the hydrodynamic force to remove the magnetically labeled and/or unlabeled non-target cells that are more weakly attached to the conduit wall, thereby further improving the target cell purity of the third mixture of cells accumulated or deposited on the conduit wall. As such, the second flow rate should be high enough to improve the purity of the magnetically labeled target cells in the third mixture of cells without substantially affecting the recovery rate thereof (when compared to the target cell population in the first fluid sample). For example, a higher second flow rate may be used for a magnetic separator device that generates higher field gradient, and/or target cells having higher density of targeted antigen, and/or larger magnetic beads that have higher magnetic moment when magnetized.

After passage of the second fluid sample through the magnetic separator device 188, the third mixture of non-target cells and magnetically labeled target cells deposited on the conduit wall is recovered by elution with a third buffer fluid, thereby forming a third fluid sample. Prior to flowing the third fluid sample through the magnetic separator device, the recovered third mixture of cells in the third fluid sample may be further diluted and resuspended in additional third buffer fluid. Alternatively, the elution process may be carried out by using an excess of the third buffer fluid to dilute the recovered third mixture of cells without the separate dilution step. The third buffer fluid may be same as the first buffer fluid and/or second buffer fluid.

Like the first iteration, the recovery/elution and dilution/resuspension processes for the second iteration may be carried out using the magnetic separator device 230 in the recovery position as shown in FIG. 9. The third buffer fluid may flow from the buffer fluid container 244 through the conduit 192 of the magnetic separator device 188 to flush the third mixture of cells accumulated on the conduit wall to the positive collection container 248. During the elution process, the agitator arm 240 that clutches the conduit 192 may provide transverse vibration to the conduit 192 to dissociate and loosen the third mixture of cells from the conduit wall. The dilution/resuspension process may be carried out with higher volume of third buffer fluid and without application of the transverse vibration to the conduit 192.

If the second iteration through the magnetic separation device can attain sufficiently high target cell purity, then the sorting process may stop with the recovery/elution step without further dilution/resuspension. Otherwise, the sorting process may continue by passing the third fluid sample through the magnetic separator device for a third iteration.

The third fluid sample having a third volume, which includes the third mixture of non-target cells and magnetically labeled target cells, the third buffer fluid used for elution, and additional third buffer fluid as dilutant, if any, is flowed through the conduit (e.g., 192) of the magnetic separator device (e.g., 188) for the third time at a third flow rate to deposit a fourth mixture of non-target cells and magnetically labeled target cells on the conduit wall that has a higher purity of the magnetically labeled target cells than the third mixture of cells. The third volume may be at least as high as the second volume and higher than the first volume by 10-150%, preferably 20-120%, more preferably 30-90%, and most preferably 40-70%. Therefore, the third fluid sample may have a significantly lower concentration of cells and/or biological objects than the first fluid sample owing to larger volume while containing fewer cells and/or biological objects.

Using the fluidic circuit 230 of FIG. 10 as an example, the third fluid sample may flow from the fluid sample container 246 to the magnetic separator device 188 and the depleted third fluid sample may flow from the magnetic separator device 188 to the negative collection container 250 during the sorting process. The third flow rate may be at least as high as the second flow rate and higher than the first flow rate to facilitate the further separation of the magnetically labeled target cells from the non-target cells in the third fluid sample. The ratio of the third flow rate to the first flow rate may be 100-300%, preferably 120-250%, and more preferably 140-200%. The use of a higher third flow rate, as compared to the first flow rate, may further increase the hydrodynamic force to remove the magnetically labeled and/or unlabeled non-target cells that are more weakly attached to the conduit wall, thereby further improving the target cell purity of the fourth mixture of cells accumulated or deposited on the conduit wall. As such, the third flow rate should be high enough to improve the purity of the magnetically labeled target cells without substantially affecting the recovery rate thereof (when compared to the target cell population in the first fluid sample). For example, a higher third flow rate may be used for a magnetic separator that generates higher field gradient, and/or target cells having higher density of targeted antigen, and/or larger magnetic beads that have higher magnetic moment when magnetized.

After passage of the third fluid sample through the magnetic separator device 188, the fourth mixture of non-target cells and magnetically labeled target cells is recovered by elution with a fourth buffer fluid to form a fourth fluid sample. The fourth fluid sample may be further diluted and resuspended in additional fourth buffer fluid. Alternatively, the elution process may be carried out by using an excess of the fourth buffer fluid to dilute the recovered fourth mixture of cells without the separate dilution step. The fourth buffer fluid may be same as the first buffer fluid and/or the second buffer fluid and/or the third buffer fluid.

Like the previous iterations, the recovery/elution and dilution/resuspension processes for the second iteration may be carried out using the magnetic separator device 230 in the recovery position as shown in FIG. 9. The fourth buffer fluid may flow from the buffer fluid container 244 through the conduit 192 of the magnetic separator device 188 to flush the fourth mixture of cells accumulated on the conduit wall to the positive collection container 248. During the elution process, the agitator arm 240 that clutches the conduit 192 may provide transverse vibration to the conduit 192 to dissociate and loosen the cells from the conduit wall. The dilution/resuspension process may be carried out with higher volume of fourth buffer fluid and without application of the transverse vibration to the conduit 192.

If the third iteration through the magnetic separation device can attain sufficiently high target cell purity, then the sorting process may stop with the recovery/elution step without further dilution/resuspension. Otherwise, the sorting process may continue by passing the fourth fluid sample through the magnetic separator device for at least one more iteration.

The multiple iteration magnetic sorting process as described above may be carried out using the three modules 284A-284C of the magnetic separator system 280 shown in FIG. 11 in a serial manner. Moreover, the entire process may be automated by a software installed on the computer 286 and by using a common container for the positive collection outlet of the first module 284A and the sample inlet of the second module 284B and another common container for the positive collection outlet of the second module 284B and the sample inlet of the third module 284C. This allows the second fluid sample collected at the positive collection outlet of the first module 284A to be automatically drawn into the sample inlet of the second module 284B and the third fluid sample collected at the positive collection outlet of the second module 284B to be automatically drawn into the sample inlet of the third module 284C without any manual handling.

EXAMPLES

The following examples are provided to illustrate, but not limit the invention. The recovery rate of target cells reported herein is calculated from the number of events or cells for the magnetically labeled target cells in the fluid sample after magnetic sorting divided by the number of events or cells for the magnetically labeled target cells in the first (initial) fluid sample prior to any sorting, as measured by a flow cytometer (CytoFlex, Beckman Coulter). The purity of the magnetically labeled target cells reported herein is calculated from the number of events or cells for the magnetically labeled target cells divided by the number of all events or cells in the fluid sample, as measured by the flow cytometer. The recovery/elution and dilution/resuspension steps after each deposition of cells on the conduit wall are automated as described above. The same buffer fluid (MARS® MAG Buffer, Applied Cells) is used during sample preparation and magnetic sorting process.

All examples described herein are carried out using the three modules 284A-284C of the magnetic separator system 280 shown in FIG. 11 to automate the sequential magnetic sorting steps, unless noted otherwise. Therefore, after the first (initial) fluid sample is added to the fluid sample container of the first module 284A, no manual intervention is needed until the fourth fluid sample (without dilution) exits the positive collection outlet of the third module 284C.

The sequential magnetic sorting steps begin by adding a first volume of the first (initial) fluid sample, which contains a first mixture of non-target cells and magnetically labeled target cells, to the fluid sample container for the first module 284A of the magnetic separator system 280. After drawn through the sample inlet, the first fluid sample passes through the magnetic separator device 188A of the first module 284A at a first flow rate. After passage of the first fluid sample through the magnetic separator device 188A, the holder 194A moves the conduit 192A to the recovery position (i.e., FIG. 9) with the agitator arm 240A clutching the conduit 192A. A second mixture of non-target cells and magnetically labeled target cells collected on the conduit wall is eluted with about 1.2 mL of the buffer fluid (MARS® MAG Buffer, Applied Cells) through the positive collection outlet into a container while the agitator arm 240A applies transverse vibration to the conduit 192A. The second mixture of cells in the container is further diluted with about 6 mL of the buffer fluid, thereby yielding about 7.2 mL of a second fluid sample.

The second fluid sample passes through the magnetic separator device 188B of the second module 284B at a second flow rate. A third mixture of non-target cells and magnetically labeled target cells collected on the conduit wall is eluted with about 1.2 mL of the buffer fluid while the agitator arm 240B applies transverse vibration to the conduit 192B. The third mixture of cells is further diluted with about 6 mL of the buffer fluid, thereby yielding about 7.2 mL of a third fluid sample.

The third fluid sample passes through the magnetic separator device 188C of the third module 284C at a third flow rate. A fourth mixture of non-target cells and magnetically labeled target cells collected on the conduit wall is eluted with about 1.2 mL of the buffer fluid while the agitator arm 240C applies transverse vibration to the conduit 192C, thereby yielding about 1.2 mL of a fourth or final fluid sample.

Example 1: Enrichment of CD34+ Hematopoietic Stem Cells (HSCs) from Human Cord Blood Hematopoietic stem cells (HSCs), which can produce all the other cells found in blood and treat various blood diseases, are present in human umbilical cord blood. HSCs have CD34 antigen expression and therefore can be magnetically labeled and sorted accordingly.

The sample preparation process begins by extracting the buffy coat from a human cord blood sample using centrifugation over a density gradient medium (Ficoll Paque™ Plus, Cytiva). A mononuclear cell (MNC) suspension is then prepared from the buffy coat by further centrifugation over the density gradient medium. The MNC sample (i.e., initial raw sample) is resuspended in a buffer fluid (MARS® MAG Buffer, Applied Cells) at a concentration of about 100 million cells per mL of buffer fluid. The target cells (i.e., HSCs) in the resuspended MNC sample are magnetically labeled in an indirect process by first adding a first reagent containing intermediate links directed to CD34 antigen expression (EasySep™ Human CD34 Positive Selection Cocktail, STEMCELL Technologies) to the resuspended MNC sample at a ratio of about 100 μL reagent per mL of MNC sample. The mixture is incubated for 15 min at room temperature while rocking on a mixer (Nutating Mixer, Labnet International), allowing time for the primary antibodies of the intermediate links to attach to the CD34 antigens on the target cell surface. A second reagent containing magnetic beads (EasySep™ Dextran RapidSpheres™ 50100, STEMCELL Technologies) is then added to the previously incubated mixture at a ratio of about 75 μL reagent per mL of MNC sample to attach the magnetic beads to the intermediate links. After incorporating the second reagent containing the magnetic beads, the fluid sample is allowed to incubate for 10 min at room temperature while rocking on the mixer to complete the magnetic labeling process. The magnetically labeled MNC sample is further diluted with about 3 times the volume of buffer fluid (i.e., 4-fold dilution) and gently mixed by pipetting up and down to yield the initial or first fluid sample for magnetic sorting with a concentration of about 25 million cells per mL.

Figure 12:
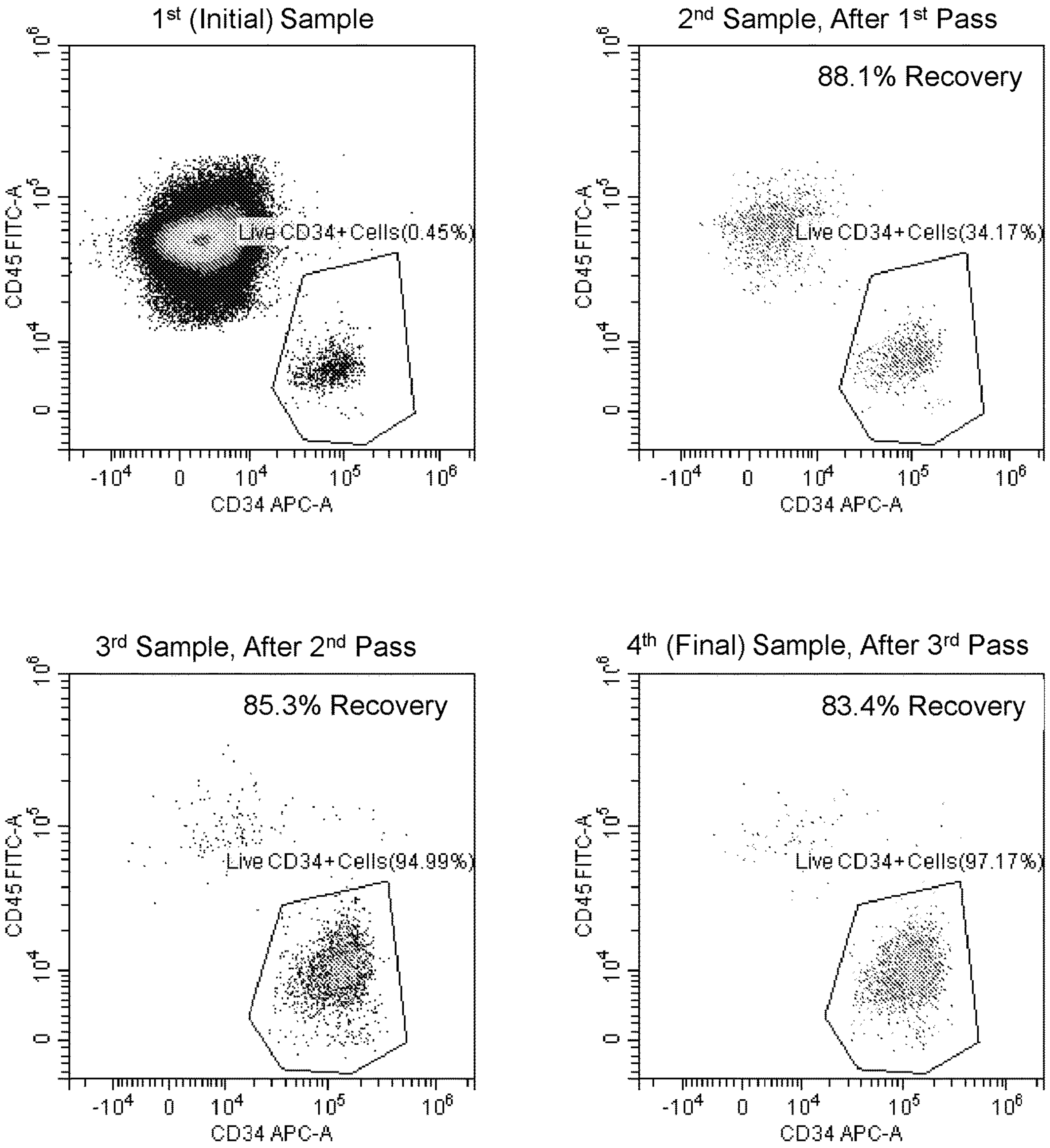
FIG. 12 shows dot plots for a PBMC sample that illustrate progression of CD34+ hematopoietic stem cell (HSC) purity before and after each magnetic sorting step.

A first volume of about 4 mL of the first (initial) fluid sample containing about 100 million total cells is used for the sequential magnetic sorting process. The first, second, and third flow rates are about 1 mL/min, 2 mL/min, and 2 mL/min, respectively. The compositions of the first (initial), second, third, and fourth (final) fluid samples are measured by the flow cytometer (CytoFlex, Beckman Coulter), as shown in the dot plots of FIG. 12. Prior to cytometry measurement, an aliquot of each of the first, second, third, and fourth fluid samples is stained with fluorescently conjugated antibodies: CD34 APC for stem cells and CD45 FITC for mononuclear cells. The cytometry results show that after sequentially passing through the three modules 284A-284C of the magnetic separator system 280, the frequency or purity of the CD34+ HSCs in the initial fluid sample increases from 0.45% to 97.17% for the final fluid sample while maintaining a high recovery rate of 83.4%.

The flow rate conditions used during magnetic sorting and cytometry results are summarized in Table I below.

TABLE I

| Sample | Flow Rate | Purity | Recovery* |
|---|---|---|---|
| 1st (Initial) Fluid Sample | | 0.45% | |
| 2nd Fluid Sample | 1 mL/min | 34.17% | 88.1% |
| 3rd Fluid Sample | 2 mL/min | 94.99% | 85.3% |
| 4th (Final) Fluid Sample | 2 mL/min | 97.17% | 83.4% |

*Recovery rate is compared to initial fluid sample as baseline

The first pass through the first module 284A at a flow rate of about 1 mL/min resulted in the second fluid sample having a purity of 34.17% and a recovery rate of 88.1%, which are achieved by the removal of ~98% of the non-target mononuclear cells in the initial fluid sample. Subsequent passes using a higher flow rate of about 2 mL/min significantly increase the purity without markedly decreasing the recovery rate.

Table II below summarizes additional experimental results for samples from different donors while using a different first flow rate of about 0.8 mL/min.

TABLE II

| Sample | Flow Rates | Initial Purity | Final Purity | Final Recovery |
|---|---|---|---|---|
| Donor #1 | 0.8/2/2 mL/min | 0.49% | 92.88% | 92.51% |
| Donor #2 | 0.8/2/2 mL/min | 0.37% | 94.91% | 80.92% |
| Donor #3 | 0.8/2/2 mL/min | 0.18% | 95.32% | 76.58% |
| Donor #4 | 0.8/2/2 mL/min | 0.88% | 98.38% | 98.86% |

The frequency or purity of the CD34+ HSCs in the initial fluid sample ranges from 0.18% to 0.88%. After automated sequential processing through the three modules 284A-284C of the magnetic separator system 280 at the flow rate conditions described above (i.e., 0.8/2/2 mL/min), the final purity exceeds 90% while the recovery rate ranges from 77% to 99%.

Example 2: Enrichment of CD138+ Plasma Cells from Bone Marrow

Plasma cells, which make antibodies to fight bacteria and virus to stop infection and disease, are made in bone marrow. Plasma cells have CD138 antigen expression and therefore can be magnetically labeled and sorted accordingly.

The sample preparation process begins by diluting a bone marrow sample with about 9 times the volume of buffer fluid (MARS® MAG Buffer, Applied Cells), i.e., 10-fold dilution. The diluted bone marrow sample is gently mixed by pipetting up and down and is then centrifuged at 300×g for 10 min with the brake off. The supernatant of the centrifuged sample is carefully removed and discarded without disturbing the cell pellet, which is resuspended with the buffer fluid to the pre-diluted sample volume.

The target cells (i.e., plasma cells) in the resuspended bone marrow sample are magnetically labeled in an indirect process by first adding a first reagent containing intermediate links directed to CD138 antigen expression (EasySep™ Human CD138 Positive Selection Cocktail, STEMCELL Technologies) to the resuspended bone marrow sample at a ratio of about 50 μL reagent per mL of bone marrow sample. The mixture is incubated for 8 min at room temperature while rocking on a mixer (Nutating Mixer, Labnet International), allowing time for the primary antibodies of the intermediate links to attach to the CD138 antigens on the target cell surface. A second reagent containing magnetic beads (EasySep™ Dextran RapidSpheres™ 50100, STEMCELL Technologies) is then added to the previously incubated mixture at a ratio of about 50 μL reagent per mL of bone marrow sample to attach the magnetic beads to the intermediate links. After incorporating the second reagent containing the magnetic beads, the fluid sample is allowed to incubate for 8 min at room temperature while rocking on the mixer to complete the magnetic labeling process. After the magnetic labeling process, the bone marrow sample is further diluted with about 9 times the volume of buffer fluid (i.e., 10-fold dilution) and gently mixed by pipetting up and down to yield the initial or first fluid sample for magnetic sorting with a concentration of about 2 million cells per mL.

Figure 13:
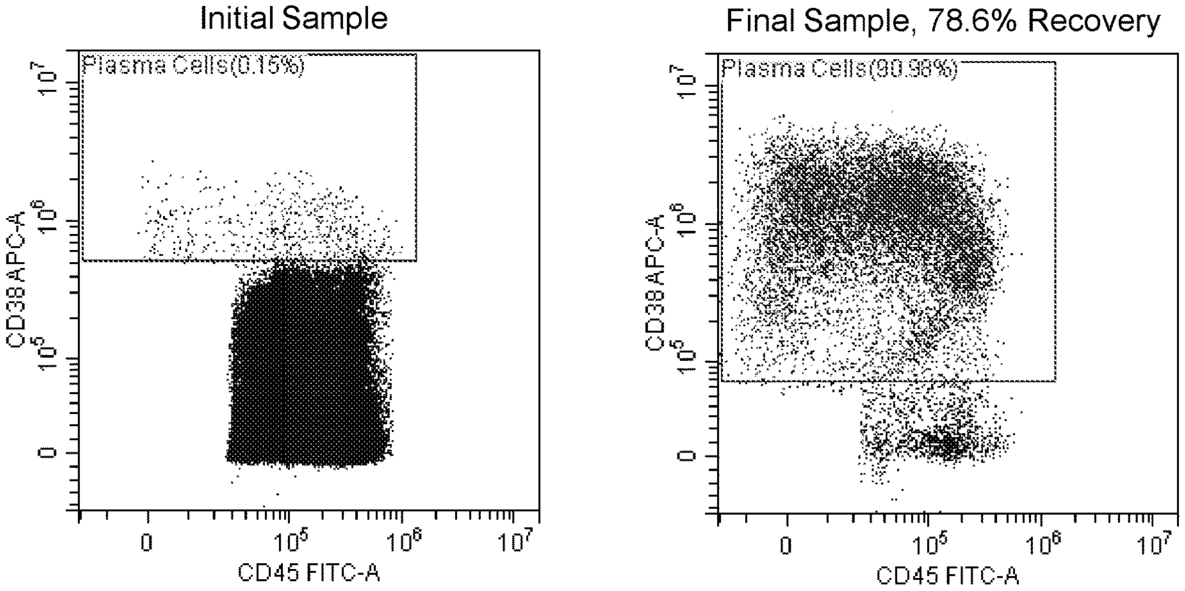
FIG. 13 shows dot plots for a bone marrow sample that illustrate purity of CD138+ plasma cells before and after sequential magnetic sorting process.

A first volume of 10 mL of the first (initial) fluid sample containing about 20 million total cells is used for the sequential magnetic sorting process. The first, second, and third flow rates are about 0.8 mL/min, 1.5 mL/min, and 1.5 mL/min, respectively. The compositions of the first (initial) sample and fourth (final) fluid samples are measured by the flow cytometer (CytoFlex, Beckman Coulter), as shown in the dot plots of FIG. 13. The cytometry results show that after sequentially passing through the three modules 284A-284C of the magnetic separator system 280 at the flow rates of about 0.8/1.5/1.5 mL/min, respectively, the frequency or purity of the plasma cells in the initial fluid sample increases from 0.15% to 90.98% for the final fluid sample while maintaining a high recovery rate of 78.6%.

Example 3: Isolation of Multiple Myeloma Cells in Whole Blood Spiked with CD138+ U266 Cells Multiple myeloma is characterized by the expansion of malignant plasma cells within the bone marrow. While these malignant plasma cells can be readily identified by their high expression of CD38 and B-$B_4$, their purification and in vitro expansion remain difficult. Therefore, established human myeloma cell lines, such as U266, are commonly used to study the biology of multiple myeloma. In this example, a peripheral blood sample is spiked with U266 cells to simulate the blood of a multiple myeloma patient.

The sample preparation process begins by staining U266 cells with fluorescently conjugated antibodies, CD298 APC (APC anti-human CD298 Antibody, Biolegend). The stained U266 cells are then added to peripheral blood and gently mixed by pipetting up and down.

The target cells (i.e., U266 cells) in the U266 spiked blood sample are magnetically labeled in an indirect process by first adding a first reagent containing intermediate links directed to CD138 antigen expression (EasySep™ Human CD138 Positive Selection Cocktail, STEMCELL Technologies) to the U266 spiked blood sample at a ratio of about 50 μL reagent per mL of blood sample. The mixture is incubated for 8 min at room temperature while rocking on a mixer (Nutating Mixer, Labnet International), allowing time for the primary antibodies of the intermediate links to attach to the CD138 antigens on the target cell surface. A second reagent containing magnetic beads (EasySep™ Dextran RapidSpheres™ 50100, STEMCELL Technologies) is then added to the previously incubated mixture at a ratio of about 50 μL reagent per mL of blood sample to attach the magnetic beads to the intermediate links. After incorporating the second reagent containing the magnetic beads, the blood sample is allowed to incubate for 8 min at room temperature while rocking on the mixer to complete the magnetic labeling process. After the magnetic labeling process, the blood sample is further diluted with about 1 time the volume of buffer fluid (i.e., 2-fold dilution) and gently mixed by pipetting up and down to yield the initial or first fluid sample for magnetic sorting with a concentration of about 2.5 million cells per mL.

Figure 14:
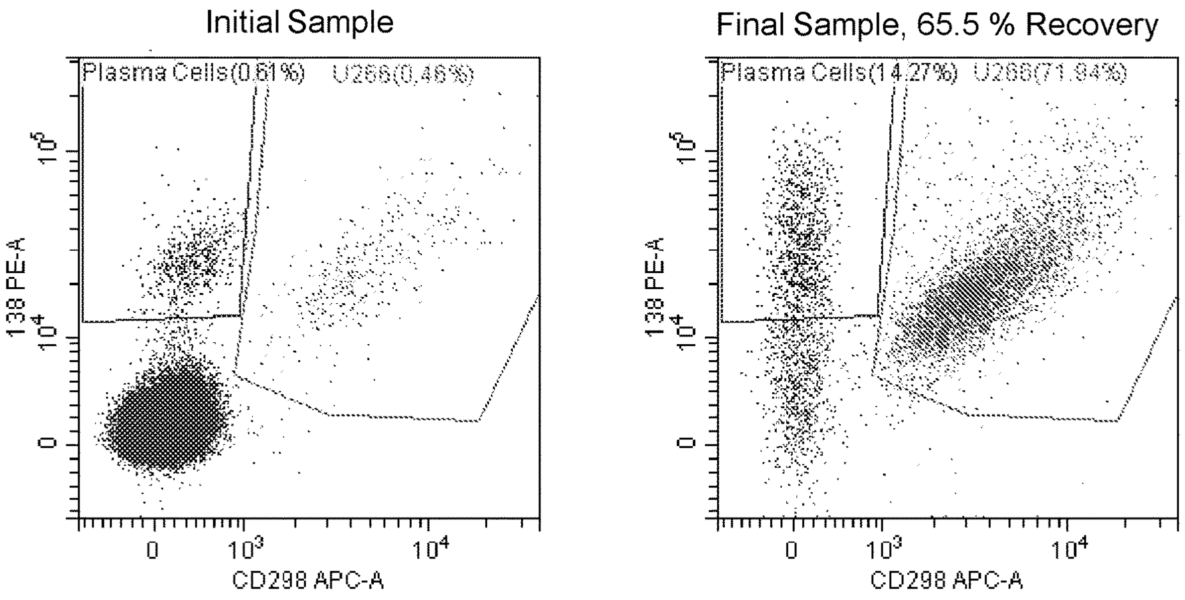
FIG. 14 shows dot plots for a peripheral blood sample spiked with U266 cells that illustrate purity of U266 cells before and after sequential magnetic sorting process.

A first volume of about 2 mL of the first (initial) fluid sample containing about 5 million total cells is used for the sequential magnetic sorting process. The first, second, and third flow rates are about 0.8 mL/min, 1.5 mL/min, and 1.5 mL/min, respectively. The compositions of the first (initial) sample and fourth (final) fluid samples are measured by the flow cytometer (CytoFlex, Beckman Coulter), as shown in the dot plots of FIG. 14. The cytometry results show that after sequentially passing through the three modules 284A-284C of the magnetic separator system 280 at the flow rates of about 0.8/1.5/1.5 mL/min, respectively, the frequency or purity of the U266 cells in the initial fluid sample increases from 0.46% to 71.94% for the final fluid sample while maintaining a high recovery rate of 65.5%.

Example 4: Isolation of Circulating Tumor Cells in Peripheral Blood Mononuclear Cell Sample Spiked with PC3 Cells Circulating tumor cells (CTCs) are cancer cells that are shed from tumors into the bloodstream. Traditional CTCs have an epithelial origin and express epithelial cellular adhesion molecule (EpCAM) marker on their surface. In this example, two peripheral blood mononuclear cell (PBMC) samples are respectively spiked with cells from a human prostate cancer cell line, PC3, at different levels: about 0.1% and 0.01%.

For each sample, the preparation process begins by staining PC3 cells with CD298 conjugated with APC (APC anti-human CD298 Antibody, Biolegend). The stained PC3 cells are then added to the PBMC sample and gently mixed by pipetting up and down. The target cells (i.e., PC3 cells) in the PBMC sample are magnetically labeled in an indirect process by first adding a first reagent containing intermediate links directed to EpCAM antigen expression and conjugated with phycoerythrin (PE) (PE anti-human CD326 (EpCAM) Antibody, Biolegend) to the PBMC sample at a ratio of about 1 μL reagent per mL of PBMC sample. The mixture is incubated for 15 min at room temperature while rocking on a mixer (Nutating Mixer, Labnet International), allowing time for the primary antibodies of the intermediate links to attach to the EpCAM antigens on the target cell surface. A second reagent containing magnetic beads (MojoSort™ Human anti-PE Nanobeads, Biolegend) is then added to the previously incubated mixture at a ratio of about 5 μL reagent per mL of PBMC sample to attach the magnetic beads to the intermediate links. After incorporating the second reagent containing the magnetic beads, the fluid sample is allowed to incubate for 20 min at room temperature while rocking on the mixer to complete the magnetic labeling process. After the magnetic labeling process, the PBMC sample is further diluted with about 1 time the volume of buffer fluid (i.e., 2-fold dilution) and gently mixed by pipetting up and down to yield the initial or first fluid sample for magnetic sorting with a concentration of about 50 million cells per mL.

For each first (initial) fluid sample, a first volume of about 2 mL containing about 100 million total cells is used for the sequential magnetic sorting process. The first, second, and third flow rates are about 0.8 mL/min, 1.0 mL/min, and 1.0 mL/min, respectively.

Figure 15:
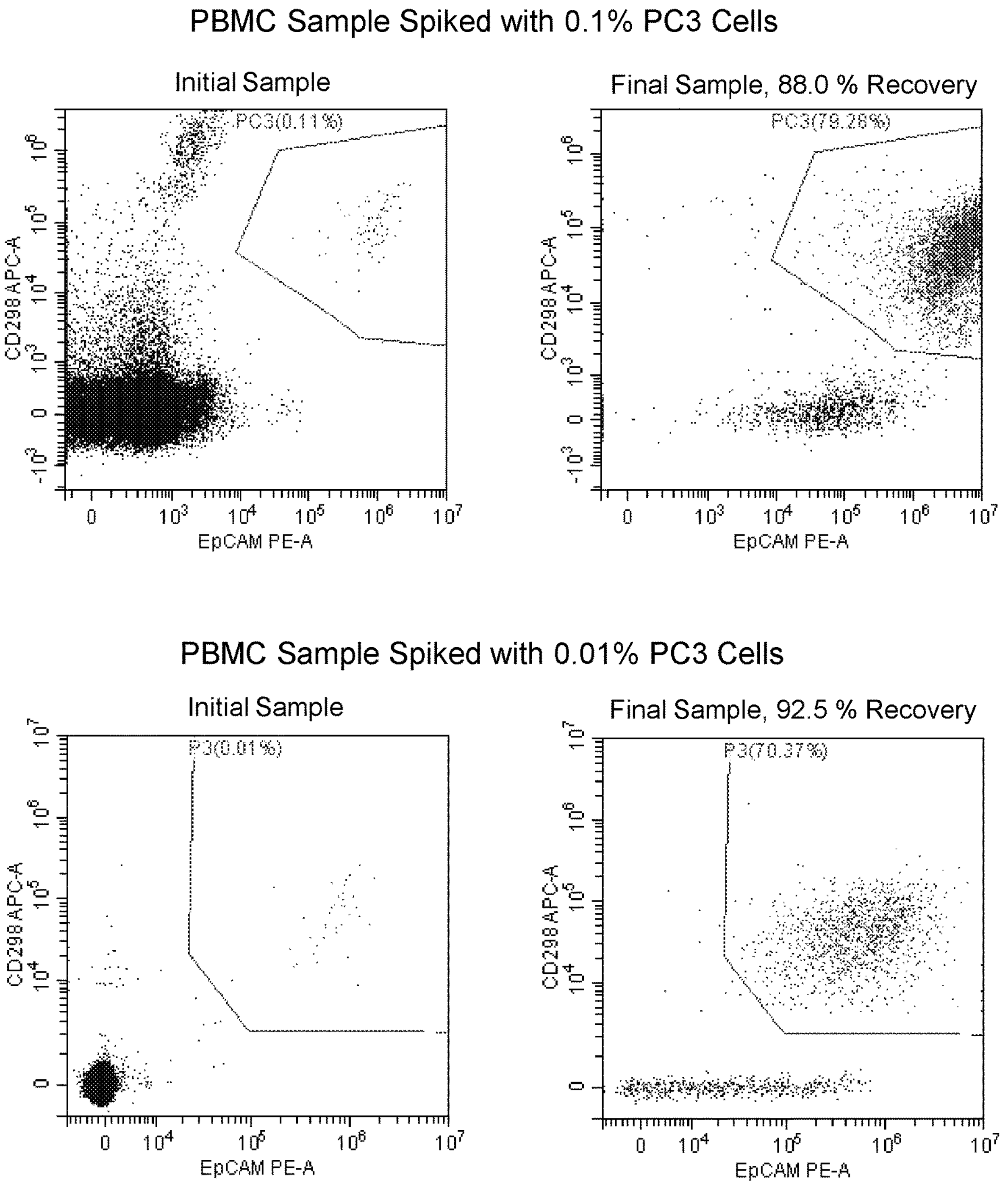
FIG. 15 shows dot plots for two PBMC samples spiked with different levels of PC3 cells that illustrate purity of PC3 cells before and after sequential magnetic sorting process.

FIG. 15 shows the cytometry results of the PBMC samples spiked with 0.11% and 0.01% PC3 cells before and after the sequential magnetic sorting process. For the sample spiked with 0.11% PC3 cells, the purity or frequency increases from 0.11% to 79.28% while maintaining a high recovery rate of 88.0% after magnetic sorting. For the sample spiked with 0.01% PC3 cells, the purity or frequency increases from 0.01% to 70.37% while maintaining a high recovery rate of 92.5% after magnetic sorting.

While the present invention has been shown and described with reference to certain preferred embodiments, it is to be understood that those skilled in the art will no doubt devise certain alterations and modifications thereto which nevertheless include the true spirit and scope of the present invention. Thus the scope of the invention should be determined by the appended claims and their legal equivalents, rather than by examples given.

Any element in a claim that does not explicitly state "means for" performing a specified function, or "step for" performing a specific function, is not to be interpreted as a "means" or "step" clause as specified in 35 U.S.C. § 112, 16. In particular, the use of "step of" in the claims herein is not intended to invoke the provisions of 35 U.S.C. § 112, 16.

What is claimed is:

1. A method for magnetically sorting rare cells including the steps of:

providing a first fluid sample containing a first mixture of non-target and magnetically labeled target cells;

flowing the first fluid sample unimpeded through a first conduit of a first magnetic separator device at a first flow rate to deposit on a conduit wall of the first conduit a second mixture of non-target and magnetically labeled target cells having a higher purity of the magnetically labeled target cells than the first mixture of non-target and magnetically labeled target cells;

recovering the second mixture of non-target and magnetically labeled target cells deposited on the conduit wall of the first conduit by eluting with a first buffer fluid to form a second fluid sample;

flowing the second fluid sample unimpeded through a second conduit of a second magnetic separator device at a second flow rate to deposit on a conduit wall of the second conduit a third mixture of non-target and magnetically labeled target cells having a higher purity of the magnetically labeled target cells than the second mixture of non-target and magnetically labeled target cells;

recovering the third mixture of non-target and magnetically labeled target cells deposited on the conduit wall of the second conduit by eluting with a second buffer fluid to form a third fluid sample;

flowing the third fluid sample unimpeded through a third conduit of a third magnetic separator device at a third flow rate to deposit on a conduit wall of the third conduit a fourth mixture of non-target and magnetically labeled target cells having a higher purity of the magnetically labeled target cells than the third mixture of non-target and magnetically labeled target cells; and recovering the fourth mixture of non-target and magnetically labeled target cells deposited on the conduit wall of the third conduit by eluting with a third buffer fluid, wherein the second flow rate is greater than or equal to the first flow rate, the third flow rate is greater than or equal to the second flow rate and is greater than the first flow rate.

2. The method of claim 1, wherein the second and third flow rates are equal and are greater than the first flow rate.

3. The method of claim 1, wherein the magnetically labeled target cells express CD34 antigen.

4. The method of claim 1, wherein the magnetically labeled target cells are magnetically labeled hematopoietic stem cells that express CD34 antigen.

5. The method of claim 1, wherein the magnetically labeled target cells express CD138 antigen.

6. The method of claim 1, wherein the magnetically labeled target cells are magnetically labeled plasma cells that express CD138 antigen.

7. The method of claim 1, wherein the magnetically labeled target cells express EpCAM antigen.

8. The method of claim 1, wherein the magnetically labeled target cells are circulating tumor cells that express EpCAM antigen.

9. The method of claim 1, wherein a frequency of the magnetically labeled targets cells in the first mixture of non-target and magnetically labeled target cells is at most 1%.

10. The method of claim 1, wherein a frequency of the magnetically labeled targets cells in the first mixture of non-target and magnetically labeled target cells is at most 0.1%.

11. The method of claim 1, wherein the first fluid sample has a lower volume than the second and third fluid samples.

12. The method of claim 1, wherein the second and third fluid samples have the same volume.

13. The method of claim 1, wherein during the steps of recovering the first, second, and third mixtures of non-target and magnetically labeled target cells, the first, second, and third conduits are subjected to transverse vibration.

14. The method of claim 1, wherein the first, second, and third magnetic separator devices each comprise:

a respective one of the first, second, and third conduits;

a holder that supports the respective one of the first, second, and third conduits; and a magnetic assembly for applying a magnetic field to the respective one of the first, second, and third conduits.

15. The method of claim 14, wherein the first, second, and third magnetic separator devices each further comprise an arm with a fork end operably clutching the respective one of the first, second, and third conduits to apply transverse vibration to the respective one of the first, second, and third conduits.

16. The method of claim 14, wherein during the steps of recovering the first, second, and third mixtures of non-target and magnetically labeled target cells, the first, second, and third conduits each are removed from the magnetic field.

17. The method of claim 14, wherein the magnetic assembly comprises:

first and second permanent magnets each having first and second poles;

a center magnetic flux guide including a center tip having a tapering shape and a center base magnetically coupled to the first poles of the first and second permanent magnets;

a first side magnetic flux guide including a first side tip and a first side base magnetically coupled to the second pole of the first permanent magnet; and a second side magnetic flux guide including a second side tip and a second side base magnetically coupled to the second pole of the second permanent magnet, wherein the first and second side magnetic flux guides are disposed on opposite sides of the center magnetic flux guide with the first and second side tips positioned above the center tip and pointed at each other.

18. The method of claim 17, wherein the first and second side tips have a first magnetic polarity and the center tip has a second magnetic polarity opposite to the first magnetic polarity.

19. The method of claim 17, wherein ends of the first and second side tips each have a chisel edge profile with a bevel side facing away from the center magnetic flux guide.

20. The method of claim 19, wherein during the steps of flowing the first, second, and third fluid samples, a ridge structure of the holder pushes the respective one of the first, second, and third conduits into a gap delineated by a tip end of the center tip and the bevel sides of the first and second side tips.

* * * * *